US006946116B2

(12) United States Patent
Kung et al.

(10) Patent No.: US 6,946,116 B2
(45) Date of Patent: *Sep. 20, 2005

(54) AMYLOID PLAQUE AGGREGATION INHIBITORS AND DIAGNOSTIC IMAGING AGENTS

(75) Inventors: Hank F. Kung, Wynnewood, PA (US); Mei-Ping Kung, Wynnewood, PA (US); Zhi-Ping Zhuang, Lansdale, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/739,217

(22) Filed: Dec. 19, 2003

(65) Prior Publication Data

US 2004/0131545 A1 Jul. 8, 2004

Related U.S. Application Data

(63) Continuation of application No. 10/127,678, filed on Apr. 23, 2002, now Pat. No. 6,696,039.
(60) Provisional application No. 60/285,282, filed on Apr. 23, 2001.

(51) Int. Cl.$^7$ .............................................. A61M 36/14
(52) U.S. Cl. .................... 424/1.89; 424/1.11; 424/1.65; 424/1.81; 424/1.85; 544/235; 548/300.1
(58) Field of Search .............................. 424/1.11, 1.65, 424/1.81, 1.85, 1.89, 9.1, 9.2, 9.3, 9.4, 9.5, 9.6, 9.7, 9.8; 534/7, 10–16; 548/300.1, 301.7, 302.7; 540/1; 544/224, 233, 235, 180, 182, 183

(56) References Cited

U.S. PATENT DOCUMENTS

| 5,869,500 A | 2/1999 | Trottmann et al. |
| 6,037,473 A | 3/2000 | Dilk et al. |
| 6,168,776 B1 | 1/2001 | Klunk et al. |
| 6,696,039 B2 | 2/2004 | Kung et al. |

FOREIGN PATENT DOCUMENTS

| EP | 0 659 418 A1 | 6/1995 |
| WO | WO 95/06469 A1 | 3/1995 |
| WO | WO 97/41856 A1 | 11/1997 |
| WO | WO 98/17267 A1 | 4/1998 |
| WO | WO 99/24394 A2 | 5/1999 |
| WO | WO 02/085903 A2 | 10/2002 |

OTHER PUBLICATIONS

Ashburn, T.T., et al., "Amyloid probes based on Congo Red distinguish between fibrils comprising different peptides," *Chem. Biol.* 3:351–358, Current Biology, Ltd. (1996).
Berge, S.M., et al., "Pharmaceutical Salts," *J. Pharm. Sci.* 66: 1–19, American Pharmaceutical Association (1977).
Bottin–Strzalko, T., and Seyden–Penne, J., "La réaction de Wittig–Horner á partir de phosphonate benzylique permet–elle la synthése de stilbéne cis ?" *Bull. Soc. Chim. Fr.* (3–4, Pt. 2):161–163, Bayeaux Société Francaise De Chimie (1984).
Bottin–Strzalko, T., and Seyden–Penne, J., "Could cis–stilbene be prepared from benzylic phosphonate by a Wittig–Horner reaction?" CAplus, Accession No. 1984:570794 (1984).
Dezutter, N.A., et al., "Preparation and biological evaluation of technetium–99m–L,L–propylenedicysteine," *J. Labelled Cpd. Radiopharm.* 42:553–565, John Wiley & Sons, Ltd. (1999).
Dezutter, N.A., et al., "$^{99m}$Tc–MAMA–chrysamine G, a probe for beta–amyloid protein of Alzheimer's disease," *Eur. J. Nucl. Med.* 26:1392–1399, Springer–Verlag (1999).
Elhaddaoui, A., et al., "Competition of Congo Red and Thioflavin S Binding to Amyloid Sites in Alzheimer's Diseased Tissue," *Biospectroscopy* 1:351–356, John Wiley & Sons, Ltd. (1995).
Filler, R. et al., "Synthesis of fluorovinylsalicylic acids and their derivatives," *J. Fluor. Chem.* 74:69–75, Elsevier (1995).
Findeis, M.A., "Approaches to discovery and characterization of inhibitors of amyloid β–peptide polymerization," *Biochim. Biophys. Acta* 1502:76–84, Elsevier Science B.V.(Jul. 2000).
Ginsberg, S.D., et al., "Molecular Pathology of Alzheimer's Disease and Related Disorders," in *Cereb. Cortex*, Peters, A., and Morrison, J.H., eds., Kluwer Academic/Plenum Publishers, New York, NY, pp. 603–654 (1999).
Golde, T.E., et al., "Biochemical detection of Aβ isoforms: implicaitions for pathogenesis, diagnois, and treatment of Alzheimer's disease," *Biochim. Biophys. Acta* 1502:172–187, Elsevier Science B.V. (Jul. 2000).
Han, H., et al., "Technetium Complexes for the Quantitation of Brain Amyloid," *J. Am. Chem. Soc.* 118:4506–4507, American Chemical Society (1996).
Katz, T.J., et al., "Synthesis and Properties of Optically Active Helical Metallocene Oligomers," *J. Am. Chem. Soc.* 115:3182–3198, American Chemical Society (1993).
Klunk, W.E. et al., "Quantitative Evaluation of Congo Red Binding to Amyloid–like Proteins with a Beta–pleated Sheet Conformation," *J. Histochem. Cytochem.* 37:1273–1281, Histochemical Society, Inc. (1989).

(Continued)

Primary Examiner—Dameron L. Jones
(74) Attorney, Agent, or Firm—Sterne, Kessler, Goldstein & Fox P.L.L.C.

(57) ABSTRACT

This invention relates to a method of imaging amyloid deposits and to labeled compounds, and methods of making labeled compounds useful in imaging amyloid deposits. This invention also relates to compounds, and methods of making compounds for inhibiting the aggregation of amyloid proteins to form-amyloid deposits, and a method of delivering a therapeutic agent to amyloid deposits.

16 Claims, 2 Drawing Sheets

OTHER PUBLICATIONS

Klunk, W.E., et al., "Quantitative in vitro NMR analysis of Alzheimer's, non–Alzheimer's demented and control brain," *Biol. Psychiatry (Abstracts)* 35:627, Abstract No. 44, Elsevier (1994).

Klunk, W.E., et al., "Chrysamine–G Binding to Alzheimer and Control Brain: Autopsy Study of a New Amyloid Probe," *Neurobiol. Aging* 16:541–548, Elsevier Science, Ltd. (1995).

Klunk, W.E., et al., "Staining of AD and Tg2576 mouse brain with X–34, a highly fluorescent derivative of chrysamine G and a potential in vivo probe for β–sheet fibrils," *Abstr. Soc. Neurosci.* 23:1638, Abstract No. 636.12, Society for Neuroscience (1997).

Kuner, P., et al., "Controlling Polymerization of β–Amyloid and Prion–derived Peptides with Synthetic Small Molecular Ligands," *J. Biol. Chem.* 275:1673–1678, American Society for Biochemistry and Molecular Biology, Inc. (Jan. 2000).

Kung, M.-P., et al., "Characterization of [$^{123}$I]IDAM as a novel single–photon emission tomography tracer for serotonin transporters," *Eur. J. Nucl. Med.* 26:844–853, Springer–Verlag (1999).

Kurihara, A., and Pardridge, W.M., "Aβ$^{1-40}$ Peptide Radiopharmaceuticals for Brain Amyloid Imaging: $^{111}$In Chelation, Conjugation to Poly(ethylene glycol)–Biotin Linkers, and Autoradiography with Alzheimer's Disease Brain Sections," *Bioconjug. Chem.* 11:380–386, American Chemical Society (May/Jun. 2000).

Lin, A.J., and Kasina, S., "Synthesis of 3–Substituted 7–(3, 3–Dimethyl–1–triazeno)–10–methylphenothiazines as Potential Antitumor Agents," *J. Heterocycl. Chem.* 18:759–761, HeteroCorporation (1981).

Lorenzo, A., and Yankner, B.A., "β–Amyloid neurotoxicity requires fibril formation and is inhibited by Congo red," *Proc. Natl. Acad. Sci. USA* 91:12243–12247, National Academy Press (1994).

Mathis, C.A., et al., "Synthesis of a lipophilic, radioiodinated ligand with high affinity to amyloid protein in Alzheimer's disease brain tissue," *J. Labelled Cpd. Radiopharm.* 40:94–95, John Wiley & Sons, Ltd. (1997).

Mital, R.L., and Jain, S.K., "Synthesis of Some 5–Substituted 2–Aminobenzenethiols and their Conversion into Phenothiazines via Smiles Rearrangement," *J. Chem. Soc. (C)* 16:2148–2150, Royal Society of Chemistry (1969).

Moore, C.L. et al., "Difluoro Ketone Peptidomimetics Suggest a Large S1 Pocket for Alzheimer's γ–Secretase: Implications for Inhibitor Design," *J. Med. Chem.* 43:3434–3442, American Chemical Society (Sep. 2000).

Näslund, J., et al., "Correlation Between Elevated Levels of Amyloid β–Peptide in the Brain and Cognitive Decline," *JAMA* 283:1571–1577, American Medical Association (Mar. 2000).

Selkoe, D.J., "Biology of β–Amyloid Precursor Protein and the Mechanism of Alzheimer Disease," in *Alzheimer Disease*, Terry, R.D., et al., eds., Lippincott Williams & Wilkens, Philadelphia, PA, pp. 293–310 (1999).

Selkoe, D.J., "The Origins of Alzheimer Disease. A is for Amyloid," *JAMA* 283:1615–1617, American Medical Association (Mar. 2000).

Selkoe, D.J., "Imaging Alzheimer's amyloid," *Nat. Biotechnol.* 18:823–824, Nature Publishing Company (Aug. 2000).

Skovronsky, D.M., and Lee, V. M.-Y., "β–Secretase revealed: starting gate for race to novel therapies for Alzheimer's disease," *Trends Pharmacol. Sci.* 21:161–163, Elsevier (May 2000).

Skovronsky, D.M., et al., "In vivo detection of amyloid plaques in a mouse model of Alzheimer's disease," *Proc. Natl. Acad. Sci. USA* 97:7609–7614, National Acadamy Press (Jun. 2000).

Stevens, M.F.G., et al., "Structural Studies on Bioactive Compounds. 23. Synthesis of Polyhydroxylated 2–Phenylbenzothiazoles and a Comparison of Their Cytotoxicites and Pharmacological Properties with Genistein and Quercetin," *J. Med. Chem.* 37:1689–1695, American Chemical Society (1994).

Styren, S.D., et al., "X–34, A Fluorescent Derivative of Congo Red: A Novel Histochemical Stain for Alzheimer's Disease Pathology," *J. Histochem. Cytochem.* 48:1223–1232, Histochemical Society, Inc. (Sep. 2000).

Tanaka, A., et al., "Inhibitors of Acyl–CoA:Cholesterol O–Acyltransferase. 2. Identification and Structure–Activity Relationships of a Novel Series of N–Alky-N–(heteroaryl-substituted benzyl)–N'–arylurease," *J. Med. Chem.* 41:2390–2410, American Chemical Society (1998).

Twyman, L.J., and Allsop, D., "A Short Synthesis of the β–amyloid (Aβ) Aggregation Inhibitor 3–ρ–Toluoyl–2–[4'–(3–diethylaminopropoxy)–phenyl]–benzofuran.," *Tetrahedron Lett.* 40:9383–9384, Elsevier Science, Ltd. (1999).

Vassar, R., et al., "β–Secretase Cleavage of Alzheimer's Amyloid Precursor Protein by the Transmembrane Aspartic Protease BACE," *Science* 286:735–741, American Association for the Advancement of Science (1999).

Vogelsberg–Ragaglia, V., et al., "Cell Biology of Tau and Cytoskeletal Pathology Alzheimer Disease," in *Alzheimer Disease*, 2$^{nd}$ edition, Terry, R.D., et al., ads., Lippincott Williams & Wilkins, Philadelphia, PA, pp. 359–372 (1999).

Wengenack, T.M., et al., "Targeting Alzheimer amyloid plaques in vivo," *Nat. Biotechnol.* 18:868–872, Nature Publishing Company (Aug. 2000).

Wolfe, M.S., et al., "A Substrate–Based Difluoro Ketone Selectively Inhibits Alzheimer's γ–Secretase Activity," *J. Med. Chem.* 41:6–9, American Chemical Society (1998).

Xia, W., et al., "Presenilin complexes with the C–terminal fragments of amyloid precursor protein at the sites of amyloid β–protein generation," *Proc. Natl. Acad. Sci. USA* 97:9299–9304, National Academy Press (Aug. 2000).

Zhen, W., et al., "Synthesis and Amyloid Binding Properties of Rhenium Complexes: Preliminary Progress Toward a Reagent for SPECT Imaging of Alzhelmer's Disease Brain," *J. Med. Chem.* 42:2805–2815, American Chemical Society (1999).

Zhuang, Z.-P., et al., "IBOX(2–(4'–dimethylaminophenyl)–6–iodobenzoxazole): a ligand for imaging amyloid plaques in the brain," *Nucl. Med. Biol.* 28:887–894, Elsevier Science, Inc. (Nov. 2001).

International Search Report for International Application No. PCT/US02/12626, mailed on Nov. 13, 2002, The Hague, Netherlands.

AMYLOID PLAQUE AGGREGATION INHIBITORS AND DIAGNOSTIC IMAGING AGENTS

CROSS REFERENCE TO RELATED APPLICATIONS

This application is a continuation of U.S. patent application Ser. No. 10/127,678, filed Apr. 23, 2002, now U.S. Pat. No. 6,696,039, which claims the benefit of U.S. Provisional Application No. 60/285,282, filed Apr. 23, 2001, the contents of which are entirely incorporated by reference herein.

STATEMENT REGARDING FEDERALLY-SPONSORED RESEARCH AND DEVELOPMENT

Part of the work performed during development of this invention utilized U.S. Government funds. The U.S. Government has certain rights in this invention under grant numbers NS-18509 and PO1 AG-11542 awarded by the Institute for the Study of Aging.

BACKGROUND OF THE INVENTION

1. Field of the Invention

This invention relates to novel bioactive compounds, methods of diagnostic imaging using radiolabeled compounds, and methods of making radiolabeled compounds.

2. Background Art

Alzheimer's disease (AD) is a progressive neurodegenerative disorder characterized by cognitive decline, irreversible memory loss, disorientation, and language impairment. Postmortem examination of AD brain sections reveals abundant senile plaques (SPs) composed of amyloid-$\beta$ (A$\beta$) peptides and numerous neurofibrillary tangles (NFTs) formed by filaments of highly phosphorylated tau proteins (for recent reviews and additional citations see Ginsberg, S. D., et al., "Molecular Pathology of Alzheimer's Disease and Related Disorders," in *Cerebral Cortex: Neurodegenerative and Age-related Changes in Structure and Function of Cerebral Cortex*, Kluwer Academic/Plenum, NY (1999), pp. 603–654; Vogelsberg-Ragaglia, V., et al., "Cell Biology of Tau and Cytoskeletal Pathology in Alzheimer's Disease," *Alzheimer's Disease*, Lippincot, Williams & Wilkins, Philadelphia, Pa. (1999), pp. 359–372). Familial AD (FAD) is caused by multiple mutations in the A precursor protein (APP), presenilin 1 (PS1) and presenilin 2 (PS2) genes (Ginsberg, S. D., et al., "Molecular Pathology of Alzheimer's Disease and Related Disorders," in *Cerebral Cortex: Neurodegenerative and Age-related Changes in Structure and Function of Cerebral Cortex*, Kluwer Academic/Plenum, NY (1999), pp. 603–654; Vogelsberg-Ragaglia, V., et al., "Cell Biology of Tau and Cytoskeletal Pathology in Alzheimer's Disease," *Alzheimer's Disease*, Lippincot, Williams & Wilkins, Philadelphia, Pa. (1999), pp. 359–372).

While the exact mechanisms underlying AD are not fully understood, all pathogenic FAD mutations studied thus far increase production of the more amyloidogenic 42–43 amino-acid long form of the AP peptide. Thus, at least in FAD, dysregulation of A$\beta$ production appears to be sufficient to induce a cascade of events leading to neurodegeneration. Indeed, the amyloid cascade hypothesis suggests that formation of extracellular fibrillar A$\beta$ aggregates in the brain may be a pivotal event in AD pathogenesis (Selkoe, D. J., "Biology of B-amyloid Precursor Protein and the Mechanism of Alzheimer's Disease," *Alzheimer's Disease*, Lippincot Williams & Wilkins, Philadelphia, Pa. (1999), pp. 293–310; Selkoe, D. J., *J. Am. Med. Assoc.* 283:1615–1617 (2000); Naslund, J., et al., *J. Am. Med. Assoc.* 283:1571–1577 (2000); Golde, T. E., et al., *Biochimica et Biophysica Acta* 1502:172–187 (2000)).

Various approaches in trying to inhibit the production and reduce the accumulation of fibrillar A$\beta$ in the brain are currently being evaluated as potential therapies for AD (Skovronsky, D. M. and Lee, V. M., *Trends Pharmacol. Sci.* 21:161–163 (2000); Vassar, R., et al., *Science* 286:735–741 (1999); Wolfe, M. S., et al., *J. Med. Chem.* 41:6–9 (1998); Moore, C. L., et al., *J. Med. Chem.* 43:3434–3442 (2000); Findeis, M. A., *Biochimica et Biophysica Acta* 1502:76–84 (2000); Kuner, P., Bohrmann, et al., *J. Biol. Chem.* 275:1673–1678 (2000)). It is therefore of great interest to develop ligands that specifically bind fibrillar A$\beta$ aggregates. Since extracellular SPs are accessible targets, these new ligands could be used as in vivo diagnostic tools and as probes to visualize the progressive deposition of A$\beta$ in studies of AD amyloidogenesis in living patients.

To this end, several interesting approaches for developing fibrillar AP aggregate-specific ligands have been reported (Ashburn, T. T., et al., *Chem. Biol.* 3:351–358 (1996); Han, G., et al., *J. Am. Chem. Soc.* 118:4506–4507 (1996); Klunk, W. E., et al., *Biol. Psychiatry* 35:627 (1994); Klunk, W. E., et al., *Neurobiol. Aging* 16:541–548 (1995); Klunk, W. E., et al., *Society for Neuroscience Abstract* 23:1638 (1997); Mathis, C. A., et al., *Proc. XIIth Intl. Symp. Radiopharm. Chem., Uppsala, Sweden*:94–95 (1997); Lorenzo, A. and Yankner, B. A., *Proc. Natl. Acad. Sci. U.S.A.* 91:12243–12247 (1994); Zhen, W., et al., *J. Med. Chem.* 42:2805–2815 (1999)). The most attractive approach is based on highly conjugated chrysamine-G (CG) and Congo red (CR), and the latter has been used for fluorescent staining of SPs and NFTs in postmortem AD brain sections (Ashburn, T. T., et al., *Chem. Biol.* 3:351–358 (1996); Klunk, W. E., et al., *J. Histochem. Cytochem.* 37:1273–1281 (1989)). The inhibition constants ($K_i$) for binding to fibrillar AP aggregates of CR, CG, and 3'-bromo- and 3'-iodo derivatives of CG are 2,800, 370, 300 and 250 nM, respectively (Mathis, C. A., et al., *Proc. XIIth Intl. Symp. Radiopharm. Chem., Uppsala, Sweden*:94–95 (1997)). These compounds have been shown to bind selectively to A$\beta$ (1–40) peptide aggregates in vitro as well as to fibrillar A$\beta$ deposits in AD brain sections (Mathis, C. A., et al., *Proc. XIIth Intl. Symp. Radiopharm. Chem., Uppsala, Sweden*:94–95 (1997)).

Amyloidosis is a condition characterized by the accumulation of various insoluble, fibrillar proteins in the tissues of a patient. An amyloid deposit is formed by the aggregation of amyloid proteins, followed by the further combination of aggregates and/or amyloid proteins.

In addition to the role of amyloid deposits in Alzheimer's disease, the presence of amyloid deposits has been shown in diseases such as Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstamnn-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, and Islets of Langerhans diabetes Type II insulinoma.

Thus, a simple, noninvasive method for detecting and quantitating amyloid deposits in a patient has been eagerly sought. Presently, detection of amyloid deposits involves histological analysis of biopsy or autopsy materials. Both methods have drawbacks. For example, an autopsy can only be used for a postmortem diagnosis.

The direct imaging of amyloid deposits in vivo is difficult, as the deposits have many of the same physical properties (e.g., density and water content) as normal tissues. Attempts to image amyloid deposits using magnetic resonance imaging (MRI) and computer-assisted tomography (CAT) have been disappointing and have detected amyloid deposits only under certain favorable conditions. In addition, efforts to label amyloid deposits with antibodies, serum amyloid P protein, or other probe molecules have provided some selectivity on the periphery of tissues, but have provided for poor imaging of tissue interiors.

Potential ligands for detecting A$\beta$ aggregates in the living brain must cross the intact blood-brain barrier. Thus brain uptake can be improved by using ligands with relatively smaller molecular size (compared to Congo Red) and increased lipophilicity. Highly conjugated thioflavins (S and T) are commonly used as dyes for staining the A$\beta$ aggregates in the AD brain (Elhaddaoui, A., et al., *Biospectroscopy* 1: 351–356 (1995)). These compounds are based on benzothiazole, which is relatively small in molecular size. However, thioflavins contain an ionic quarternary amine, which is permanently charged and unfavorable for brain uptake.

Thus, it would be useful to have a noninvasive technique for imaging and quantitating amyloid deposits in a patient. In addition, it would be useful to have compounds that inhibit the aggregation of amyloid proteins to form amyloid deposits and a method for determining a compound's ability to inhibit amyloid protein aggregation.

BRIEF SUMMARY OF THE INVENTION

The present invention provides novel compounds of Formula I, II, III or III' that bind preferentially to amyloid aggregates.

The present invention also provides diagnostic compositions comprising a radiolabeled compound of Formula I, II, III or III', and a pharmaceutically acceptable carrier or diluent.

The invention further provides a method of imaging amyloid deposits, the method comprising introducing into a patient a detectable quantity of a labeled compound of Formula I, II, III or III' or a pharmaceutically acceptable salt, ester, amide, or prodrug thereof.

The present invention also provides a method for inhibiting the aggregation of amyloid proteins, the method comprising administering to a mammal an amyloid inhibiting amount of a compound Formula I, II, III or III' or a pharmaceutically acceptable salt, ester, amide, or prodrug thereof.

A further aspect of this invention is directed to methods and intermediates useful for synthesizing the amyloid inhibiting and imaging compounds of Formula I, II, III or III' described herein.

DETAILED DESCRIPTION OF THE INVENTION

Figure 1A:
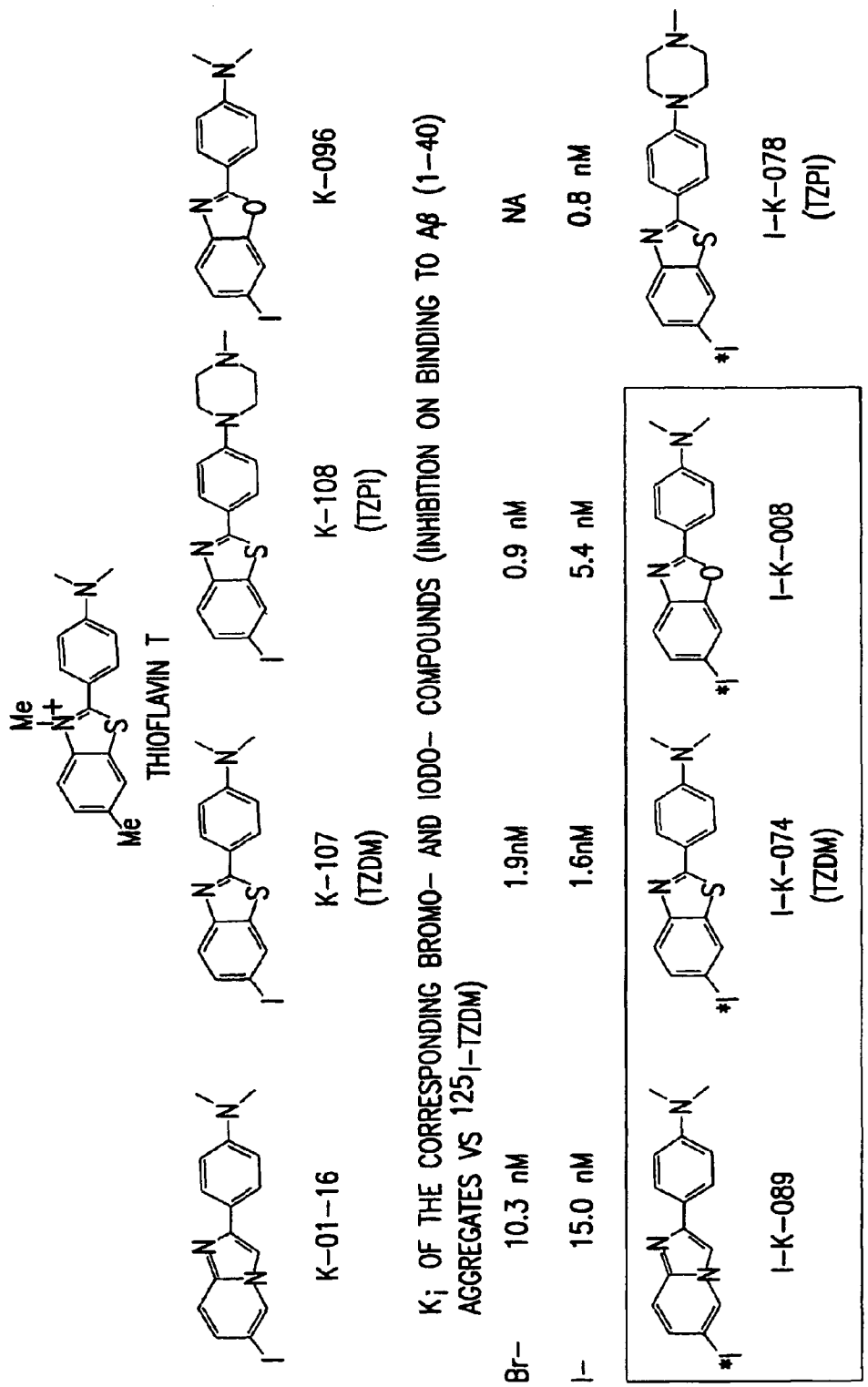
FIG. 1A and FIG. 1B depict representative compounds of the present invention and the binding data for these compounds.

A first aspect of the present invention is directed to compounds of the following Formula I:

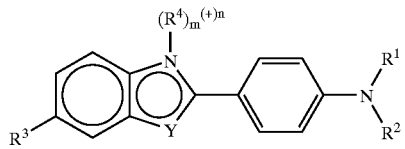

I or a pharmaceutically acceptable salt thereof,
wherein:

Y is CH, NR$^5$, O, S or CH=N, where R$^5$ is hydrogen or a C$_{1-4}$ alkyl;

m and n are both zero, or m and n are both 1;

R$^3$ is CH$_3$, Br, I, F, $^{125}$I, $^{131}$I, $^{123}$I, $^{18}$F, $^{76}$Br, $^{77}$Br or Sn(alkyl)$_3$;

R$^1$ and R$^2$ are independently hydrogen, C$_{1-4}$ alkyl, C$_{2-4}$ aminoalkyl, C$_{1-4}$ haloalkyl, haloarylalkyl, -L-Ch, or R$^1$ and R$^2$ are taken together with the nitrogen to which they are attached to form a 5- to 7-member heterocyclic ring optionally having O, S or NR$^6$ in said ring, where R$^6$ is hydrogen or C$_{1-4}$ alkyl; and R$^4$ is C$_{1-4}$ alkyl; and L is a covalent bond or a linking group, such as —(CH$_2$)$_n$—, or —(CH$_2$), —C(O)— where n is 1–5; and Ch is a tetradentate ligand capable of complexing with a metal, such as a ligand selected from the group consisting of:

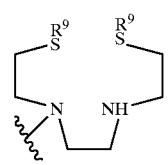

IV

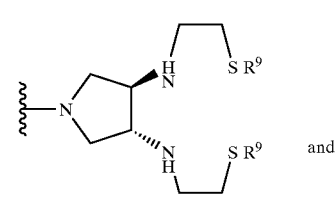

V and

-continued

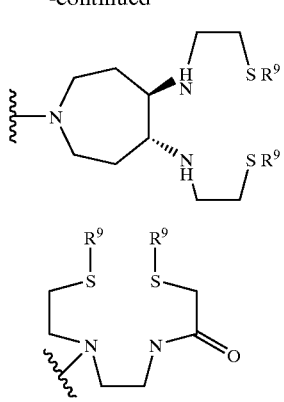

where $R^9$ is hydrogen or a sulfur protecting group, such as methoxymethyl, methoxyethoxymethyl, p-methoxybenzyl or benzyl, and the other variable groups have the preferred values mentioned herein.

In this embodiment, compounds having Ch ligands, such as those of Formulae VIII, IX, X and XI are complexed with 99m-pertechnetate, as described herein to form metal chelates where Ch is selected from the group consisting of:

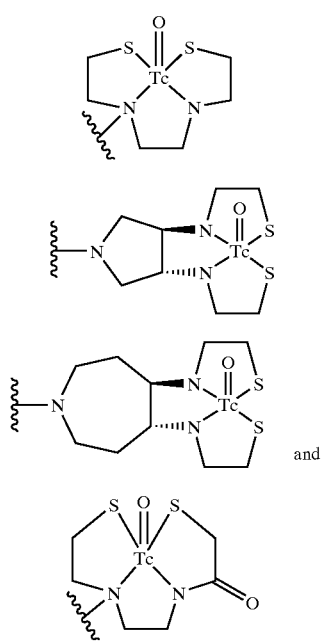

Additionally, a rhenium radioisotope can be complexed with the Ch ligand.

A preferred group of compounds falling within the scope of the present invention include compounds of Formula I wherein Y is selected from $NR^5$, O or S. Especially preferred compounds of Formula I include compounds wherein Y is $NR^5$ or S, most preferably Y is S.

Preferred values of $R^5$ in compounds of Formula I where Y is $NR^5$ are hydrogen and $C_{1-4}$ alkyl, more preferably $R^5$ is hydrogen or methyl, and most preferably $R^5$ is hydrogen.

A preferred value of m and n in compounds of Formula I is from zero to one, more preferably zero.

Suitable values of $R^3$ are Br, I, F, $^{125}I$, $^{131}I$, $^{123}I$, $^{18}F$, $^{76}Br$, or $^{77}Br$. Especially useful values of $R^3$ are $^{125}I$, $^{131}I$, $^{123}I$, $^{18}F$, $^{76}Br$, or $^{77}Br$, more preferably $^{123}I$, $^{131}I$, $^{76}Br$ or $^{77}Br$, and most preferably $^{123}I$. Preferred embodiments also include intermediates useful in the preparation of compounds of Formula I wherein $R^3$ is $Sn(alkyl)_3$.

Preferred compounds are those of Formula I wherein $R^1$ and $R^2$ are independently one of hydrogen, $C_{1-4}$ alkyl, $C_{1-4}$ haloalkyl, halophenyl($C_{1-4}$)alkyl, or are taken together with the nitrogen to which they are attached to form a 5- to 7-member heterocyclic ring optionally having O or $NR^6$ in said ring, where $R^6$ is hydrogen or $C_{1-4}$ alkyl. Useful values of $R^1$ and $R^2$ include, independently, hydrogen, methyl, ethyl, propyl, isopropyl, butyl, t-butyl, isobutyl, 3-fluoropropyl, 4-fluorobutyl, or 4-fluorobenzyl, or $R^1$ and $R^2$ are taken together with the nitrogen to which they are attached to form a piperidinyl ring having $NR^6$ in said ring, where $R^6$ is hydrogen or methyl.

The present invention is also directed to compounds of Formula II:

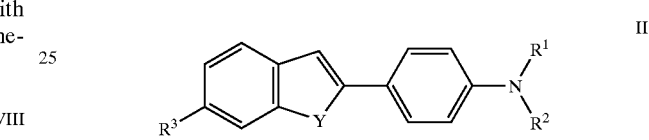

or a pharmaceutically acceptable salt thereof, wherein:

Y is O or $NR^4$ where $R^4$ is hydrogen or $C_{1-4}$ alkyl;

$R^3$ is Br, I, F, $^{125}I$, $^{131}I$, $^{123}I$, $^{18}F$, $^{76}Br$, $^{77}Br$ or $Sn(alkyl)_3$;

$R^1$ and $R^2$ are independently hydrogen, $C_{1-4}$ alkyl, $C_{2-4}$ aminoalkyl, $C_{1-4}$ haloalkyl, haloarylalkyl, or $R^1$ and $R^2$ are taken together with the nitrogen to which they are attached to form a 5- to 7-member heterocyclic ring optionally having O, S or $NR^5$ in said ring, where $R^5$ is hydrogen or $C_{1-4}$ alkyl.

A preferred group of compounds include compounds of Formula II where Y is $NR^4$ where $R^4$ is hydrogen or methyl. More preferred compounds include compounds where Y is O.

Useful values of $R^3$ are Br, I, F, $^{125}I$, $^{131}I$, $^{123}I$, $^{18}F$, $^{76}Br$, or $^{77}Br$. Especially suitable values of $R^3$ are $^{125}I$, $^{131}I$, $^{123}I$, $^{18}F$, $^{76}Br$, or $^{77}Br$, more preferably $^{123}I$, $^{131}I$, $^{76}Br$ or $^{77}Br$, and most preferably $^{123}I$. Preferred embodiments also include intermediates useful in the preparation of compounds of Formula II wherein $R^3$ is $Sn(alkyl)_3$.

Preferred compounds are those of Formula II wherein $R^1$ and $R^2$ are independently one of hydrogen, $C_{1-4}$ alkyl, $C_{1-4}$ haloalkyl, halophenyl($C_{1-4}$)alkyl, or are taken together with the nitrogen to which they are attached to form a 5- to 7-member heterocyclic ring optionally having O or $NR^6$ in said ring, where $R^6$ is hydrogen or $C_{1-4}$ alkyl. Useful values of $R^1$ and $R^2$ include, independently, hydrogen, methyl, ethyl, propyl, butyl, t-butyl, isobutyl, 3-fluoropropyl, 4-fluorobutyl, or 4-fluorobenzyl, or $R^1$ and $R^2$ are taken together with the nitrogen to which they are attached to form a piperidinyl ring having $NR^6$ in said ring, where $R^6$ is hydrogen or methyl.

The present invention is also directed to compounds of Formula III:

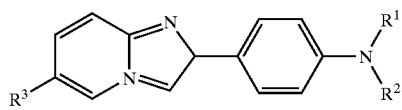

or a pharmaceutically acceptable salt thereof,
wherein:

$R^3$ is Br, I, F, $^{125}$I, $^{131}$I, $^{123}$I, $^{18}$F, $^{76}$Br, $^{77}$Br or Sn(alkyl)$_3$;

$R^1$ and $R^2$ are independently hydrogen, $C_{1-4}$ alkyl, $C_{2-4}$ aminoalkyl, $C_{1-4}$ haloalkyl, haloarylalkyl, -L-Ch, or $R^1$ and $R^2$ are taken together with the nitrogen to which they are attached to form a 5- to 7-member heterocyclic ring optionally having O, S or NR$^5$ in said ring, where $R^5$ is hydrogen or $C_4$ alkyl.

Useful values of $R^3$ are Br, I, F, $^{125}$I, $^{131}$I, $^{123}$I, $^{18}$F, $^{76}$Br, or $^{77}$Br. Especially suitable values of $R^3$ are $^{125}$I, $^{131}$I, $^{123}$I, $^{18}$F, $^{76}$Br, or $^{77}$Br, more preferably $^{123}$I, $^{131}$I, $^{76}$Br or $^{77}$Br, and most preferably $^{123}$I or $^{125}$I. Preferred embodiments also include intermediates useful in the preparation of compounds of Formula III wherein $R^3$ is Sn(alkyl)$_3$.

Preferred compounds are those of Formula III wherein $R^1$ and $R^2$ are independently one of hydrogen, $C_{1-4}$ alkyl, $C_{1-4}$ haloalkyl, halophenyl($C_{1-4}$)alkyl, or are taken together with the nitrogen to which they are attached to form a 5- to 7-member heterocyclic ring optionally having O or NR$^6$ in said ring, where $R^6$ is hydrogen or $C_{1-4}$ alkyl. Useful values of $R^1$ and $R^2$ include, independently, hydrogen, methyl, ethyl, propyl, butyl, t-butyl, isobutyl, 3-fluoropropyl, 4-fluorobutyl, or 4-fluorobenzyl, or $R^1$ and $R^2$ are taken together with the nitrogen to which they are attached to form a piperidinyl ring having NR$^6$ in said ring, where $R^6$ is hydrogen or methyl. Most preferably $R^1$ and $R^2$ are methyl.

Another preferred group of compounds are compounds of Formulae I, II, or III where $R^1$ is -L-Ch, $R^2$ is hydrogen or methyl, and $R^3$ is I or methyl. A preferred Ch is Formula IV. A preferred L is —(CH$_2$)$_n$— where n is 1, 2 or 3.

In a separate embodiment, compounds of Formula III have $R^1$ and $R^2$ groups as defined above, and $R^3$ is -L-Ch, where L and Ch are as defined above.

In another embodiment, the invention is directed to compounds of Formula III':

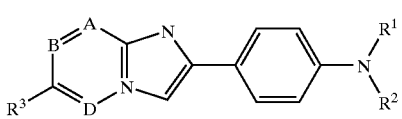

or a pharmaceutically acceptable salt thereof,
wherein:

A, B and D are CH or N, provided that no more than two of A, B and D is N;

$R^3$ is Br, I, F, $^{125}$I, $^{131}$I, $^{123}$I, $^{18}$F, $^{76}$Br, $^{77}$Br, haloalkyl or Sn(alkyl)$_3$;

$R^1$ and $R^2$ are independently hydrogen, $C_{1-4}$ alkyl, $C_{2-4}$ aminoalkyl, $C_{1-4}$ haloalkyl, haloarylalkyl, -L-Ch, or $R^1$ and $R^2$ are taken together with the nitrogen to which they are attached to form a 5- to 7-member heterocyclic ring optionally having O, S or NR$^5$ in said ring, where $R^5$ is hydrogen or $C_{1-4}$ alkyl.

Useful values of $R^3$ are Br, I, F, $^{125}$I, $^{131}$I, $^{123}$I, $^{18}$F, $^{76}$Br, $^{77}$Br or $^{18}$F/fluoro($C_{1-5}$) alkyl. Especially suitable values of $R^3$ are $^{18}$F/fluoromethyl, $^{18}$F/fluoroethyl, $^{18}$F/fluoropropyl, $^{18}$F/fluorobutyl, or $^{18}$F/fluoropentyl. Preferred embodiments also include intermediates useful in the preparation of compounds of Formula III' wherein $R^3$ is Sn(alkyl)$_3$.

In a preferred group of compounds, A and B are CH, and D is N. In another preferred group of compounds, A and D are CH, and B is N. In another preferred group of compounds, B and D are CH, and A is N.

Preferred compounds are those of Formula III' wherein $R^1$ and $R^2$ are independently one of hydrogen, $C_{1-4}$ alkyl, $C_{1-4}$ haloalkyl, halophenyl($C_{1-4}$)alkyl, or are taken together with the nitrogen to which they are attached to form a 5- to 7-member heterocyclic ring optionally having O or NR$^6$ in said ring, where $R^6$ is hydrogen or $C_{1-4}$ alkyl. Useful values of $R^1$ and $R^2$ include, independently, hydrogen, methyl, ethyl, propyl, butyl, t-butyl, isobutyl, 3-fluoropropyl, 4-fluorobutyl, or 4-fluorobenzyl, or $R^1$ and $R^2$ are taken together with the nitrogen to which they are attached to form a piperidinyl ring having NR$^6$ in said ring, where $R^6$ is hydrogen or methyl. Most preferably $R^1$ and $R^2$ are methyl.

Another preferred group of compounds are compounds of Formula I, II, III or III' where $R^1$ is -L-Ch, $R^2$ is hydrogen or methyl, and $R^3$ is 1 or methyl. A preferred Ch is Formula IV. A preferred L is —(CH$_2$)$_n$— where n is 1, 2 or 3.

In a separate embodiment, compounds of Formula III' have $R^1$ and $R^2$ groups as defined above, and $R^3$ is -L-Ch, where L is a covalent bond or linking group, such as —(CH$_2$)$_n$—, or —(CH$_2$)$_n$—C(O)— where n is 0–5, and Ch is a tetradentate ligand capable of complexing with a metal as defined above. Most preferably, L is —(CH$_2$)$_n$—, where n is 0, Ch is Formula XI, and $R^1$ and $R^2$ are independently hydrogen or $C_{1-4}$ alkyl. In this embodiment, it is most preferable that $R^1$ and $R^2$ are both methyl.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formula I, II, III, or III' may also be solvated, especially hydrated. Hydration may occur during manufacturing of the compounds or compositions comprising the compounds, or the hydration may occur over time due to the hygroscopic nature of the compounds. In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

When any variable occurs more than one time in any constituent or in Formula I, II, III or III', its definition on each occurrence is independent of its definition at every other occurrence. Also combinations of substituents and/or variables are permissible only if such combinations result in stable compounds.

Another aspect of this invention is related to methods of preparing compounds of Formula I, II, III or III'. A first method is characterized by forming a benzothiazole of Formula I wherein Y is S by reacting a 2-aminothiophenol with either: a) a 4-aminobenzaldehyde in DMSO at a temperature in the range of 100° C.–220° C., and collecting said benzothiazole; or b) a 4-halobenzoic acid derivative in a solvent in the presence of polyphosphoric acid, collecting the product of this reaction, followed by reacting said product with an amine to form said benzothiazole, and collecting said benzothiazole; and optionally reacting a benzothiazole of Formula I wherein Y is S with (alkyl)$_3$Sn in a solvent in the presence of palladiumIIoxide to form a trialkylstannyl benzothiazole, and collecting the product of this reaction; and optionally reacting a trialkylstannyl benzothiazole of Formula I wherein Y is S with either: a) iodine in a solvent at ambient temperature, and extracting the product; or b) NaI or Na[$^{125}$I]I in the presence of hydrogen peroxide, and extracting the product.

A second method is characterized by forming a benzoxazole of Formula I wherein Y is O by reacting a 2-amino-5-nitrophenol with a 4-aminobenzoic acid to form a nitro-substituted benzoxazole intermediate, and collecting said intermediate; followed by catalytic hydrogenation of said nitro group to an amino group, and collecting the product of this reaction; and reacting said product with NaNO$_2$ in the presence of H$^+$ and potassium halide to produce a benzoxazole of Formula I wherein Y is O; and optionally reacting a benzoxazole of Formula I wherein Y is O with (alkyl)$_3$Sn in a solvent in the presence of palladiumIIoxide to form a trialkylstannyl benzoxazole, and collecting the product of this reaction; and optionally reacting a trialkylstannyl benzoxazole of Formula I wherein Y is O with either: a) iodine in a solvent at ambient temperature, and extracting the product; or b) NaI or Na[$^{125}$I]I in the presence of hydrogen peroxide, and extracting the product.

A third method is characterized by forming a benzimidazole of Formula I wherein Y is N by reacting a 4-bromo-1,2-diaminobenzene with either: a) a 4-aminobenzaldehyde to form a benzimidazole of Formula I wherein Y is N, and collecting the product, or b) a 4-halobenzaldehyde to form an intermediate benzimidazole, and reacting said intermediate with a monoalkylamine, dialkylamine, or heterocyclic amine in the presence of palladiumIIoxide to form a benzimidazole of Formula I wherein Y is N, and collecting the product; and optionally reacting a benzimidazole of Formula I wherein Y is N with (alkyl)$_3$Sn in a solvent in the presence of palladiumIIoxide to form a trialkylstannyl benzimidazole, and collecting the product of this reaction; and optionally reacting a trialkylstannyl benzimidazole of Formula I wherein Y is N with either: a) iodine in a solvent at ambient temperature, and extracting the product; or b) NaI or Na[$^{125}$I]I in the presence of hydrogen peroxide, and extracting the product.

A fourth method is characterized by forming a compound of Formula I wherein R$^1$ or R$^2$ is -L-Ch. In embodiments where R$^1$ or R$^2$ is -L-Ch, the groups R$^9$ are both hydrogen, or can be any of the variety of protecting groups available for sulfur, including methoxymethyl, methoxyethoxymethyl, p-methoxybenzyl or benzyl. Sulfur protecting groups are described in detail in Greene, T. W. and Wuts, P. G. M., *Protective Groups in Organic Synthesis*, 2nd Edition, John Wiley and Sons, Inc., New York (1991).

Protecting group R$^9$ can be removed by appropriate methods well known in the art of organic synthesis, such as trifluoroacetic acid, mercuric chloride or sodium in liquid ammonia. In the case of Lewis acid labile groups, including acetamidomethyl and benzamidomethyl, R$^9$ can be left intact. Labeling of the ligand with technetium in this case will cleave the protecting group, rendering the protected diaminedithiol equivalent to the unprotected form.

Tc-99m complexes can be prepared as follows. A small amount of non-radiolabeled compound (1–2 mg) is dissolved in 100 μL EtOH and mixed with 200 μL HCl (1 N) and 1 mL Sn-glucoheptonate solution (containing 8–32 μg SnCl$_2$ and 80–320 μg Na-glucoheptonate, pH 6.67) and 50 μL EDTA solution (0.1 N). [$^{99m}$Tc]Pertechnetate (100–200 μL; ranging from 2–20 mCi) saline solution are then added. The reaction is heated for 30 min at 100° C., then cooled to room temperature. The reaction mixture is analyzed on TLC (EtOH:conc. NH$_3$ 9:1) for product formation and purity check. The mixture can be neutralized with phosphate buffer to pH 5.0.

The present invention further relates to a method of preparing a technetium-99m complex according to the present invention by reacting technetium-99m in the form of a pertechnetate in the presence of a reducing agent and optionally a suitable chelator with an appropriate Ch-containing compound.

The reducing agent serves to reduce the Tc-99m pertechnetate which is eluted from a molybdenum-technetium generator in a physiological saline solution. Suitable reducing agents are, for example, dithionite, formamidine sulphinic acid, diaminoethane disulphinate or suitable metallic reducing agents such as Sn(II), Fe(II), Cu(I), Ti(III) or Sb(III). Sn(II) has proven to be particularly suitable.

For the above-mentioned complex-forming reaction, technetium-99m is reacted with an appropriate compound of the invention as a salt or in the form of technetium bound to comparatively weak chelators. In the latter case the desired technetium-99m complex is formed by ligand exchange. Examples of suitable chelators for the radionuclide are dicarboxylic acids, such as oxalic acid, malonic acid, succinic acid, maleic acid, orthophtalic acid, malic acid, lactic acid, tartaric acid, citric acid, ascorbic acid, salicylic acid or derivatives of these acids; phosphorus compounds such as pyrophosphates; or enolates. Citric acid, tartaric acid, ascorbic acid, glucoheptonic acid or a derivative thereof are particularly suitable chelators for this purpose, because a chelate of technetium-99m with one of these chelators undergoes the desired ligand exchange particularly easily.

The most commonly used procedure for preparing [Tc$^V$O]$^{+3}$N$_2$S$_2$ complexes is based on stannous(II) chloride reduction of [$^{99m}$Tc]pertechnetate, the common starting material. The labeling procedure normally relies on a Tc-99m ligand exchange reaction between Tc-99m (Sn)-glucoheptonate and the N$_2$S$_2$ ligand. Preparation of stannous (II) chloride and preserving it in a consistent stannous(II) form is critically important for the success of the labeling reaction. To stabilize the air-sensitive stannous ion it is a common practice in nuclear medicine to use a lyophilized kit, in which the stannous ion is in a lyophilized powder form mixed with an excess amount of glucoheptonate under an inert gas like nitrogen or argon. The preparation of the lyophilized stannous chloride/sodium glucoheptonate kits ensures that the labeling reaction is reproducible and predictable. The $N_2S_2$ ligands are usually air-sensitive (thiols are easily oxidized by air) and there are subsequent reactions which lead to decomposition of the ligands. The most convenient and predictable method to preserve the ligands is to produce lyophilized kits containing 100–500 μg of the ligands under argon or nitrogen.

A fifth method is characterized by forming an isoxazole of Formula II wherein Y is O by reacting a 3-halo-2-hydroxy benzaldehyde with a substituted benzamine such as 4-(halomethyl)-benzamine to form a phenoxy benzyl ether intermediate, and collecting the intermediate; followed by reacting said intermediate in a solvent in the presence of NaOMe or NaOEt to form an isoxazole of Formula II wherein Y is O, and collecting the product; and optionally reacting an isoxazole of Formula I wherein Y is O with (alkyl)$_3$Sn in a solvent in the presence of palladiumIIoxide to form a trialkylstannyl isoxazole of Formula I wherein Y is O, and collecting the product of this reaction; and optionally reacting a trialkylstannyl isoxazole of Formula I wherein Y is O with either: a) iodine in a solvent at ambient temperature, and extracting the product; or b) NaI or Na[$^{125}$I]I in the presence of hydrogen peroxide, and extracting the product.

A sixth method is characterized by forming an indole of Formula II wherein Y is NR$^5$ by reacting a 2-nitro-4-bromo toluene with N-isopropyl-2,2'-iminodiethanol to form a N,N-dimethyl-styryl-2-nitro-4-bromo benzene intermediate, followed by reacting said intermediate with an acid chloride in the presence of triethylamine to produce an α,β-unsaturated ketone, which undergoes intramolecular annulation by heating in dioxane/water, followed by reacting with sodium hydrosulfite to form an indole of Formula II wherein Y is NR$^4$, and collecting the product; and optionally reacting said indole with methyl iodide in the presence of sodium hydride to produce an indole of Formula II wherein Y is NR$^4$ where R$^4$ is methyl, and collecting the product; and optionally reacting an indole of Formula II wherein Y is NR$^1$ with (alkyl)$_3$Sn in a solvent in the presence of palladiumIIoxide to form a trialkylstannyl indole of Formula II wherein Y is NR$^4$, and collecting the product of this reaction; and optionally reacting a trialkylstannyl indole of Formula II wherein Y is NR$^4$ with either: a) iodine in a solvent at ambient temperature, and extracting the product; or b) NaI or Na[$^{125}$I]I in the presence of hydrogen peroxide, and extracting the product.

A seventh method characterized by forming an imidazo[1,2a]pyridine of Formula III by reacting 2-amino-5-bromopyridine with either: a) a 4'-halo-1-halo-benzophenone in a solvent in the presence of sodium bicarbonate to form an intermediate imidazo[1,2a]pyridine, and collecting the product of the reaction; followed by reacting said intermediate with a monoalkylamine, dialkylamine or heterocyclic amine in the presence of palladiumIIoxide to form an imidazo[1,2a]pyridine of Formula III, or b) a 4'-amino-1-haloacetophenone in a solvent in the presence of sodium bicarbonate to form an imidazo[1,2a]pyridine of Formula III, and collecting the product of the reaction; and optionally reacting an imidazo[1,2a]pyridine of Formula III with (alkyl)$_3$Sn in a solvent in the presence of palladiumIIoxide to form a trialkylstannyl imidazo[1,2a]pyridine of Formula III, and collecting the product of this reaction; and optionally reacting a trialkylstannyl imidazo[1,2a]pyridine of Formula III with either: a) iodine in a solvent at ambient temperature, and extracting the product; or b) NaI or Na[$^{125}$I]I in the presence of hydrogen peroxide, and extracting the product.

The term "alkyl" as employed herein by itself or as part of another group refers to both straight and branched chain radicals of up to 8 carbons, preferably 6 carbons, more preferably 4 carbons, such as methyl, ethyl, propyl, isopropyl, butyl, t-butyl, and isobutyl.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 6 carbon atoms in length, more preferably 1–4 carbon atoms in length.

The term "monoalkylamine" as employed herein by itself or as part of another group refers to an amino group which is substituted with one alkyl group as defined above.

The term "dialkylamine" as employed herein by itself or as part of another group refers to an amino group which is substituted with two alkyl groups as defined above.

The term "halo" employed herein by itself or as part of another group refers to chlorine, bromine, fluorine or iodine.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heterocycle" or "heterocyclic ring", as used herein except where noted, represents a stable 5- to 7-memebered mono-heterocyclic ring system which may be saturated or unsaturated, and which consists of carbon atoms and from one to three heteroatoms selected from the group consisting of N, O, and S, and wherein the nitrogen and sulfur heteroatom may optionally be oxidized. Especially useful are rings contain one nitrogen combined with one oxygen or sulfur, or two nitrogen heteroatoms. Examples of such heterocyclic groups include piperidinyl, pyrrolyl, pyrrolidinyl, imidazolyl, imidazlinyl, imidazolidinyl, pyridyl, pyrazinyl, pyrimidinyl, oxazolyl, oxazolidinyl, isoxazolyl, isoxazolidinyl, thiazolyl, thiazolidinyl, isothiazolyl, homopiperidinyl, homopiperazinyl, pyridazinyl, pyrazolyl, and pyrazolidinyl, most preferably thiamorpholinyl, piperazinyl, and morpholinyl.

The term "heteroatom" is used herein to mean an oxygen atom ("O"), a sulfur atom ("S") or a nitrogen atom ("N"). It will be recognized that when the heteroatom is nitrogen, it may form an NR$^a$R$^b$ moiety, wherein R$^a$ and R$^b$ are, independently from one another, hydrogen or $C_{1-4}$ alkyl, $C_{2-4}$ aminoalkyl, $C_{1-4}$ halo alkyl, halo benzyl, or R$^1$ and R$^2$ are taken together to form a 5- to 7-member heterocyclic ring optionally having O, S or NR$^c$ in said ring, where R$^c$ is hydrogen or $C_{1-4}$alkyl.

The present invention is further directed to a methods of preparing compounds of the above Formula I, II III or III'. The compounds of this invention can be prepared by reactions described in Schemes 1–13.

Schemes 1 and 2 depict a synthetic route for forming benzothiazoles of Formula I. Heating 5-bromo-2-aminobenzenethiol (Mital, R. L. and Jain, S. K., *J Chem Soc (C)*:2148 (1969); Lin, A.-J. and Kasina, S., *J Heterocycl Chem* 18:759 (1981)) and 4-dimethylaminobenzaldehyde or 4-(4-methylpiperazin-1-yl)benzaldehyde (Tanaka, A., et al., *J. Med. Chem.* 41:2390 (1998)) in DMSO produced benzothiazoles, 1 and 4. Using the same Pd(0)-catalyzed Br to tributyltin exchange reaction, these two bromo derivatives were successfully converted to the corresponding tributyltin derivatives 2 and 5. They were successfully used in an iododestannylation reaction to produce the corresponding iodinated compounds 3 and 6 (yields were between 25–35%; the reactions were not optimized). Thus, the tributyltin derivatives served two useful purposes, i) they served as intermediates for converting bromo to iodo derivatives; ii) they are also useful as starting material for preparation of radioiodinated "hot" ligand.

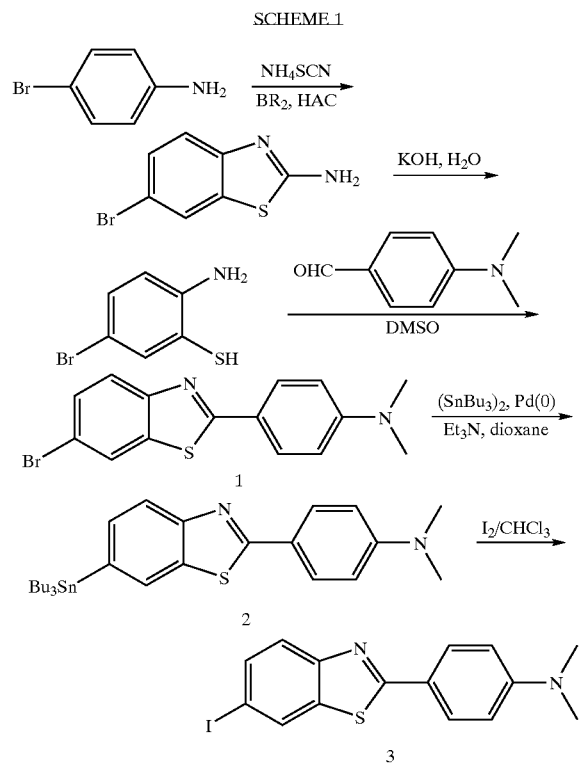

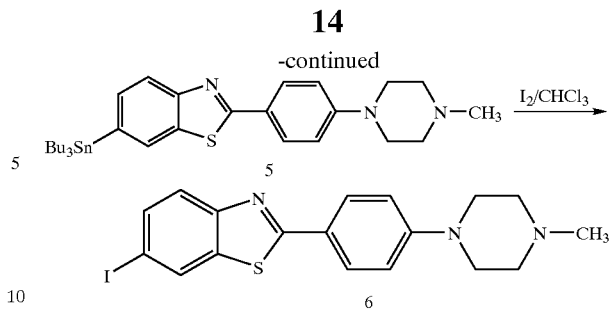

Scheme 3 depicts a synthetic route in which N-monomethylated amines are prepared, and thereafter employed in the parallel synthesis of disubstituted aminophenyl benzothiazole derivatives.

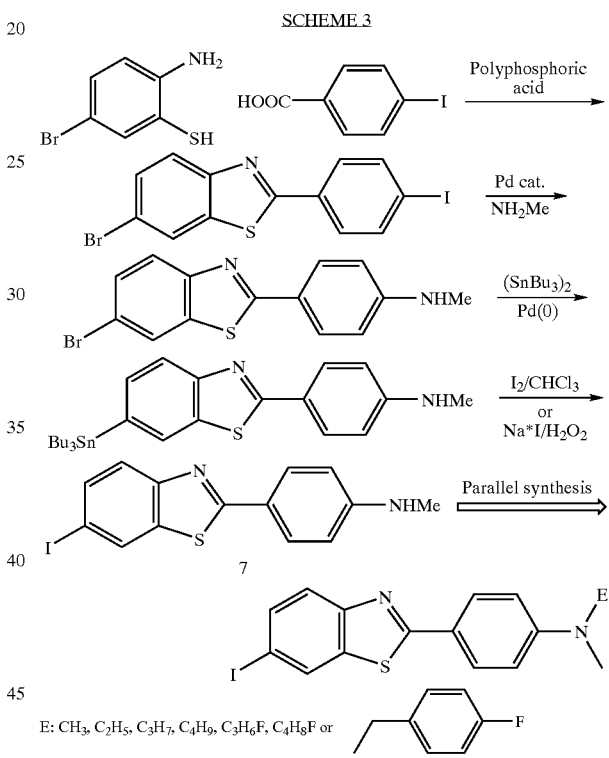

Schemes 4 through 6 depict synthetic routes for forming benzoxazoles of the present invention.

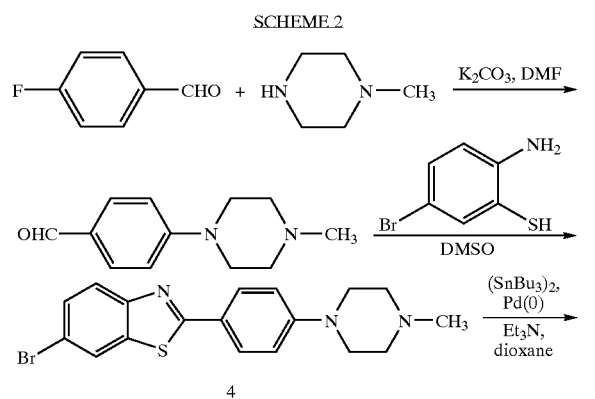

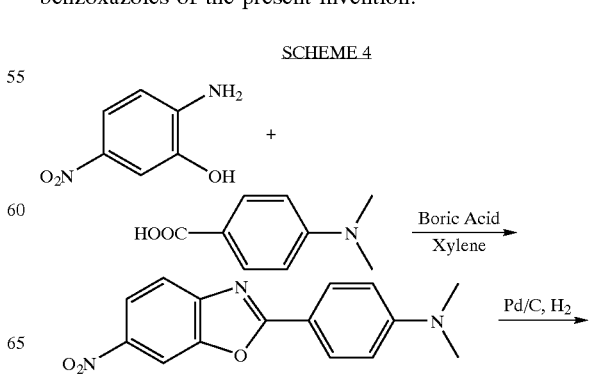

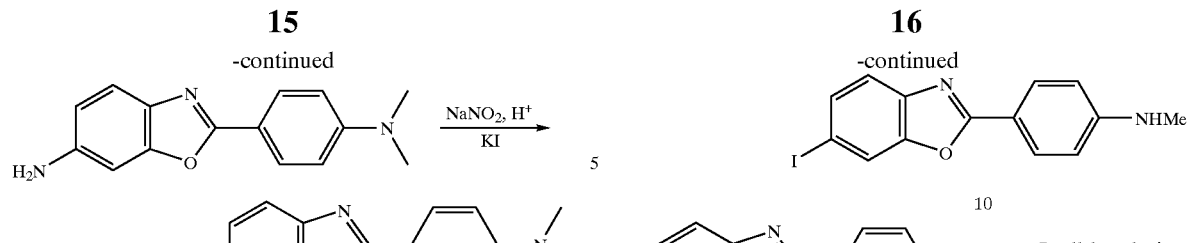
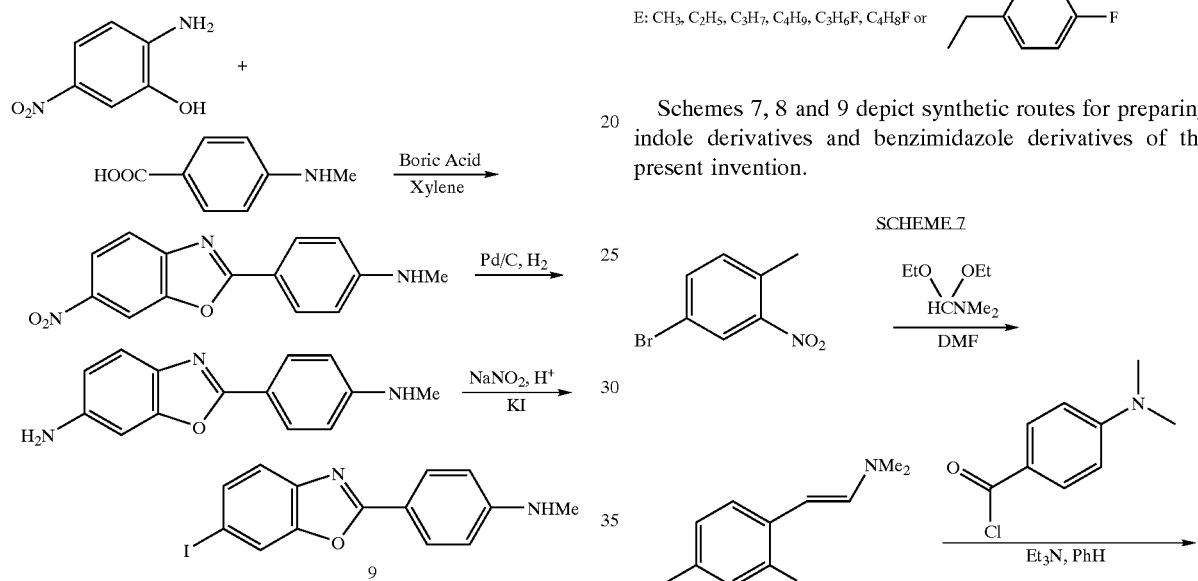
Schemes 7, 8 and 9 depict synthetic routes for preparing indole derivatives and benzimidazole derivatives of the present invention.
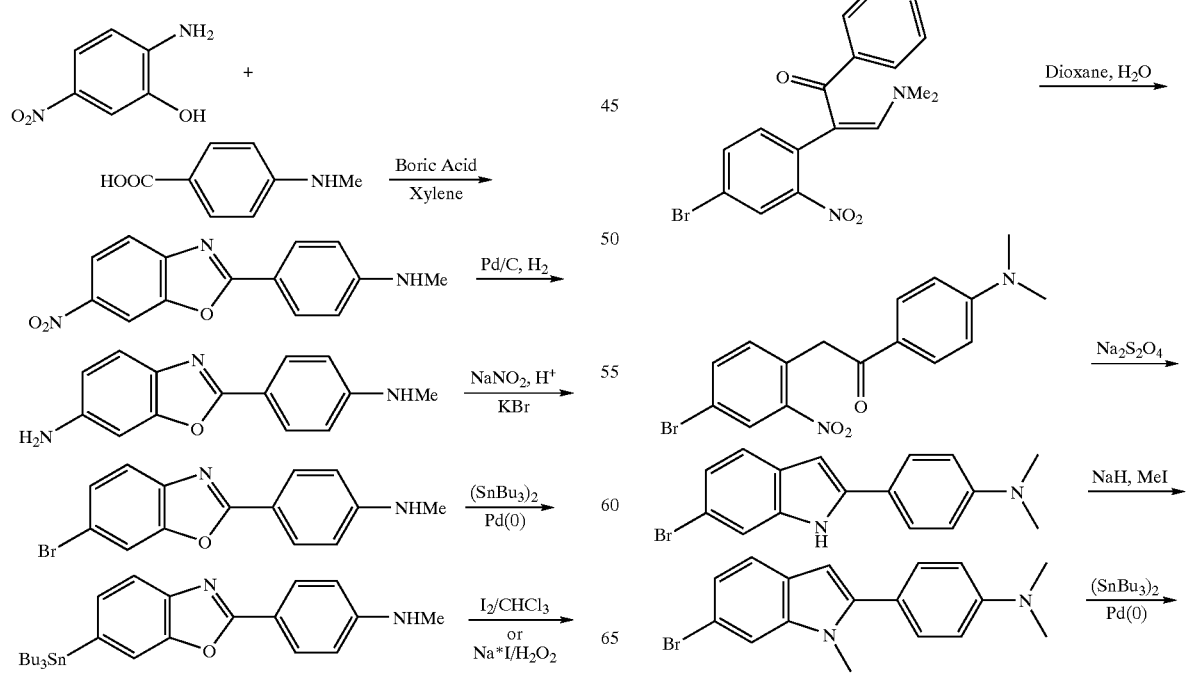

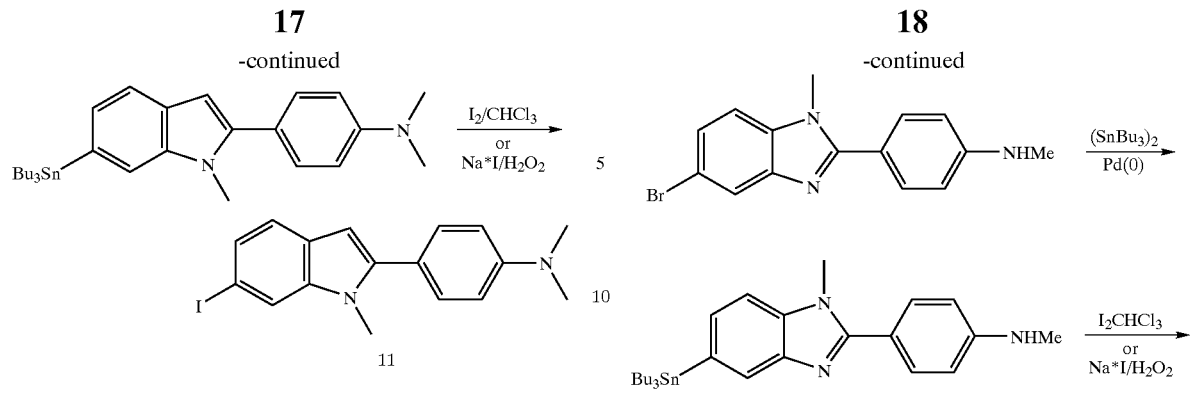
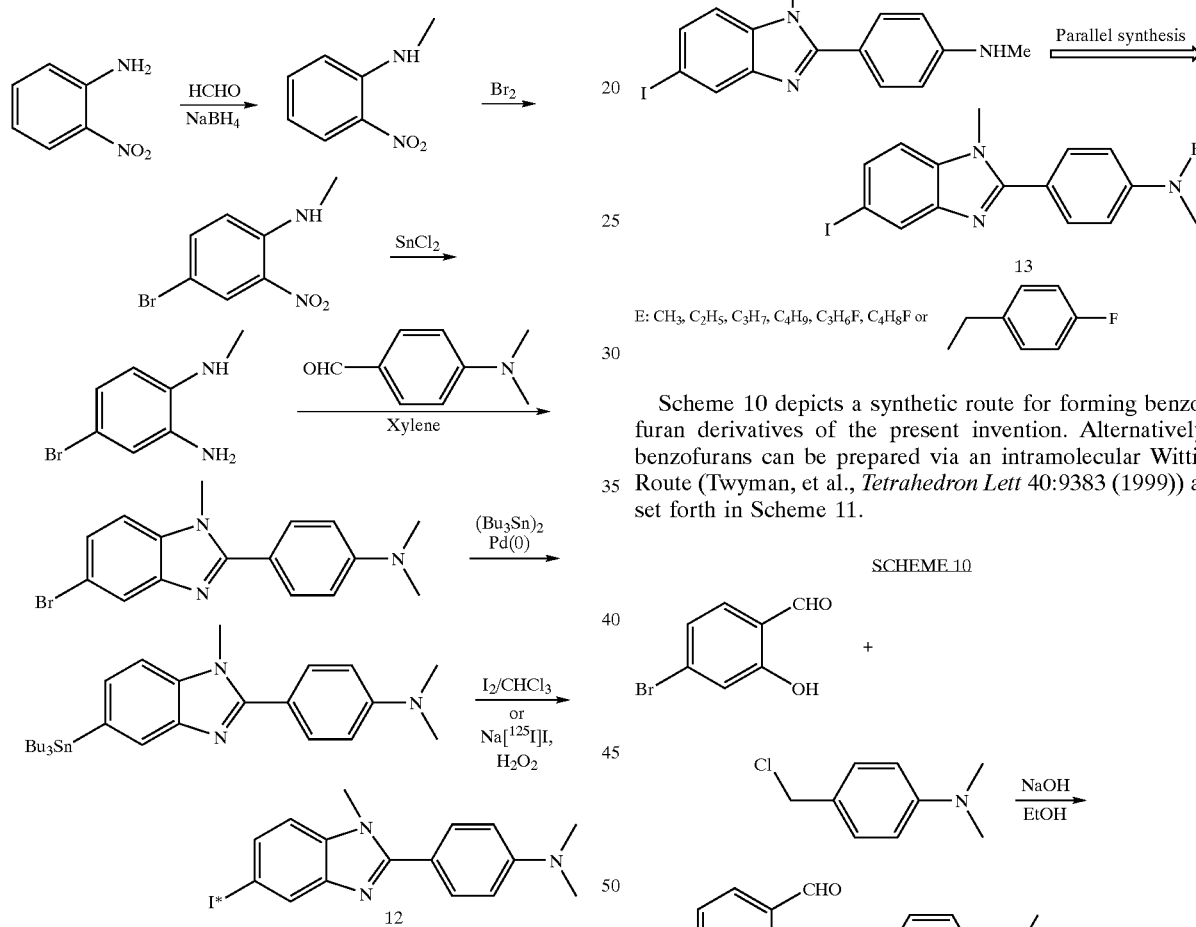
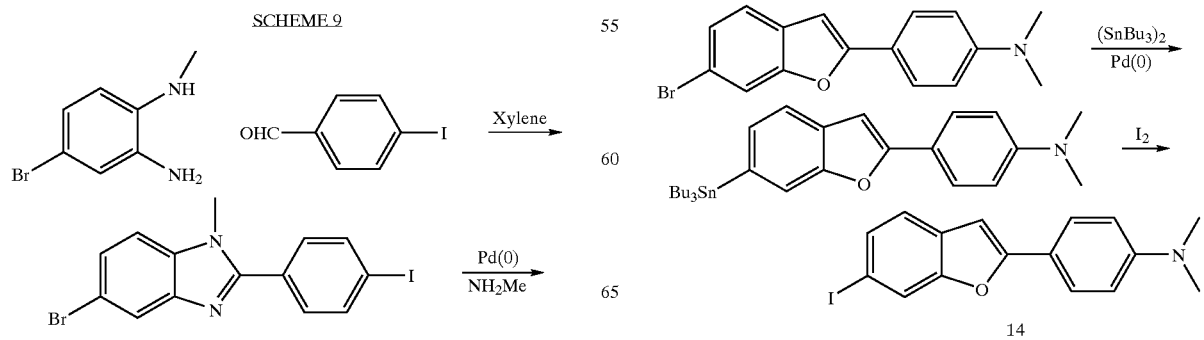
Scheme 10 depicts a synthetic route for forming benzofuran derivatives of the present invention. Alternatively, benzofurans can be prepared via an intramolecular Wittig Route (Twyman, et al., *Tetrahedron Lett* 40:9383 (1999)) as set forth in Scheme 11.

SCHEME 11
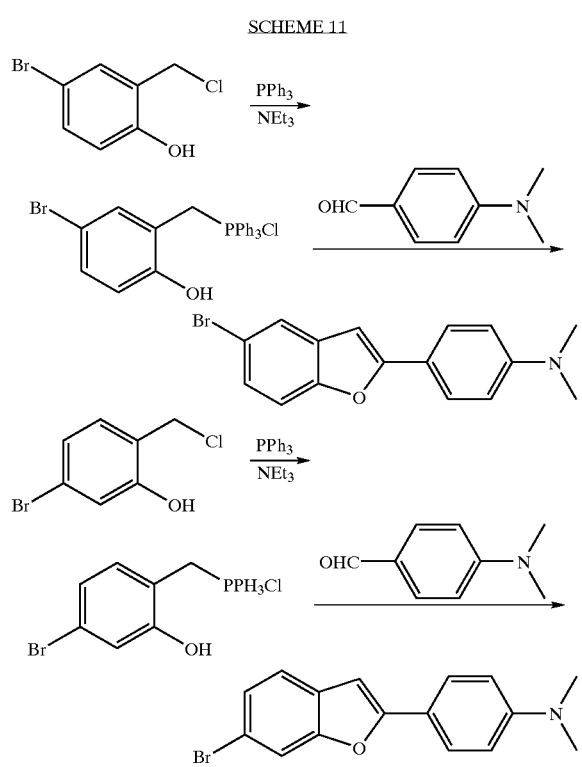
Scheme 12 provides a synthetic route for parallel synthesis of benzofuran derivatives of the present invention.
SCHEME 12
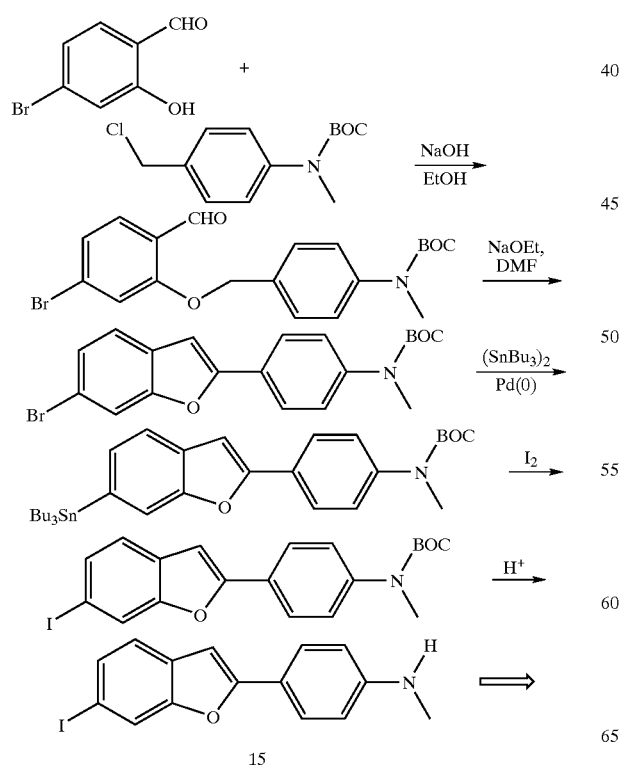
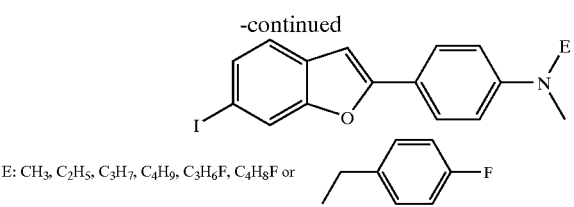
E: $CH_3$, $C_2H_5$, $C_3H_7$, $C_4H_9$, $C_3H_6F$, $C_4H_8F$ or [4-fluorobenzyl]
Schemes 13 through 17 are directed to imidazo[1,2,a]pyridine derivatives of the present invention.
SCHEME 13
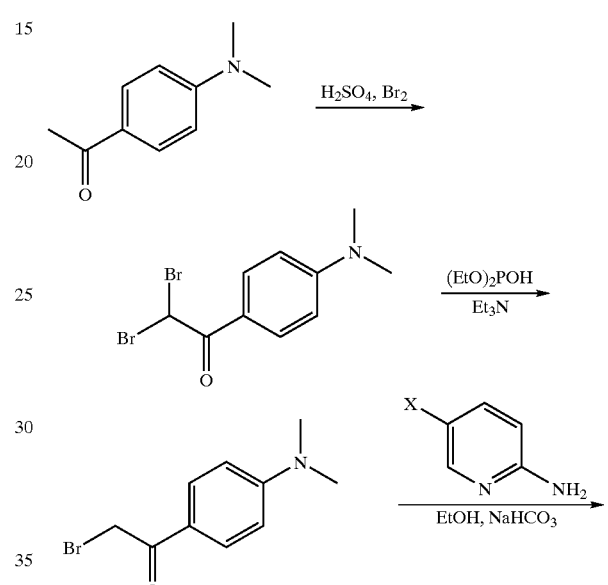
SCHEME 14
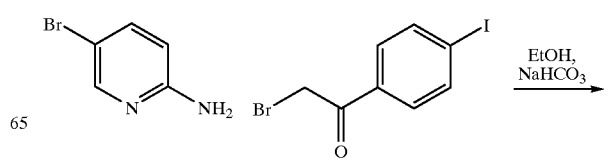

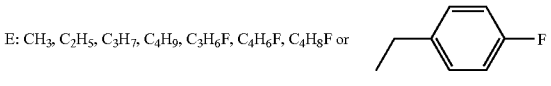
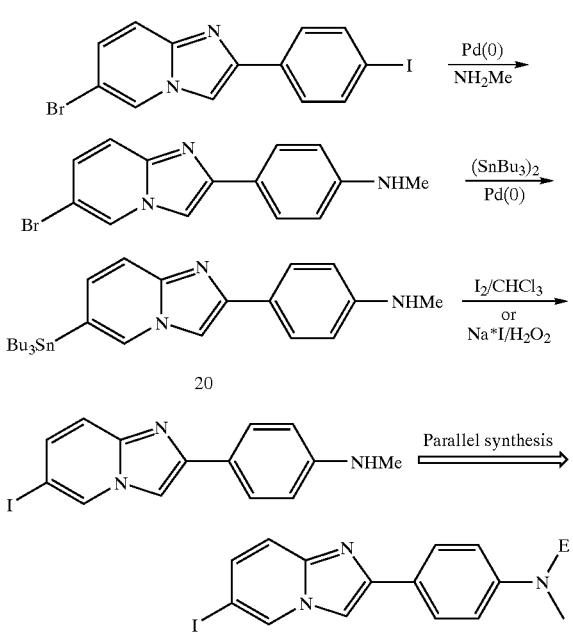
SCHEME 15
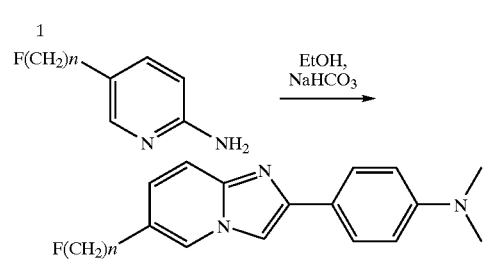
SCHEME 16
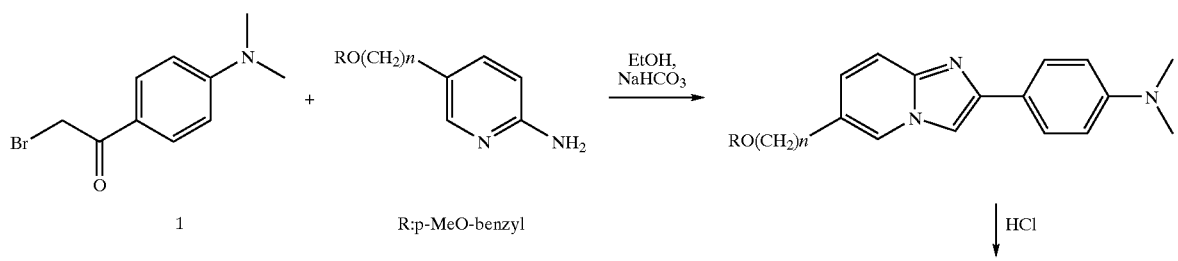
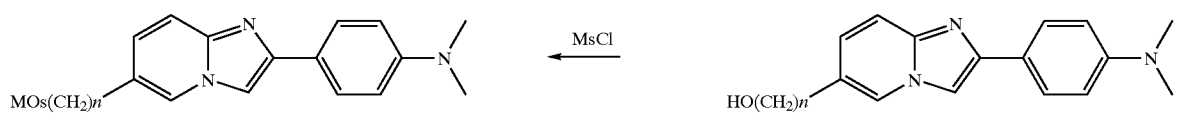
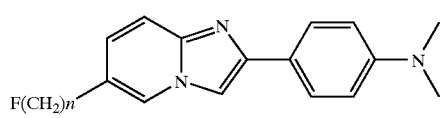
n = 1–5

SCHEME 17
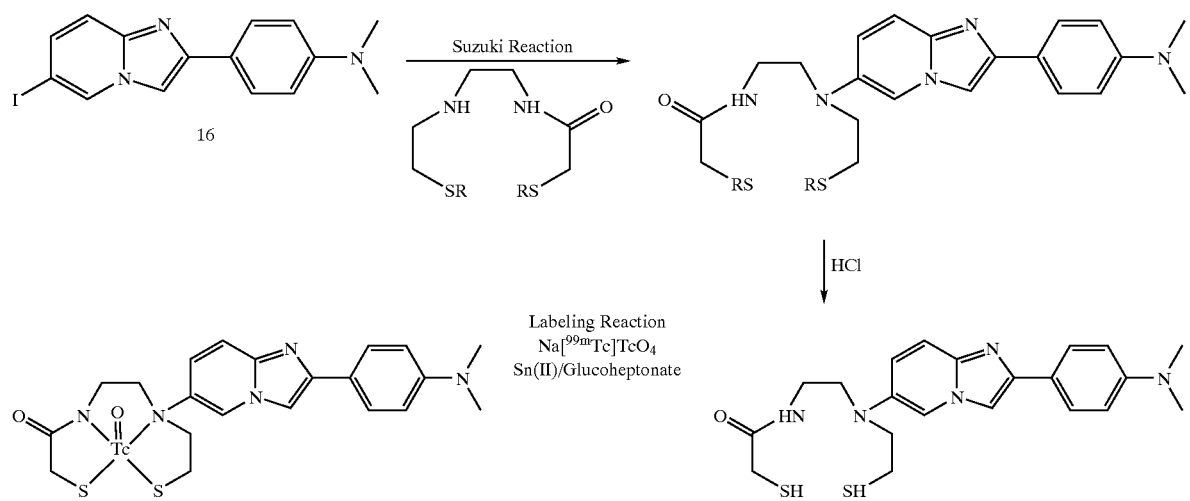
Schemes 18 and 19 depict synthetic routes for forming benzopyrimidines of the present invention.
SCHEME 18
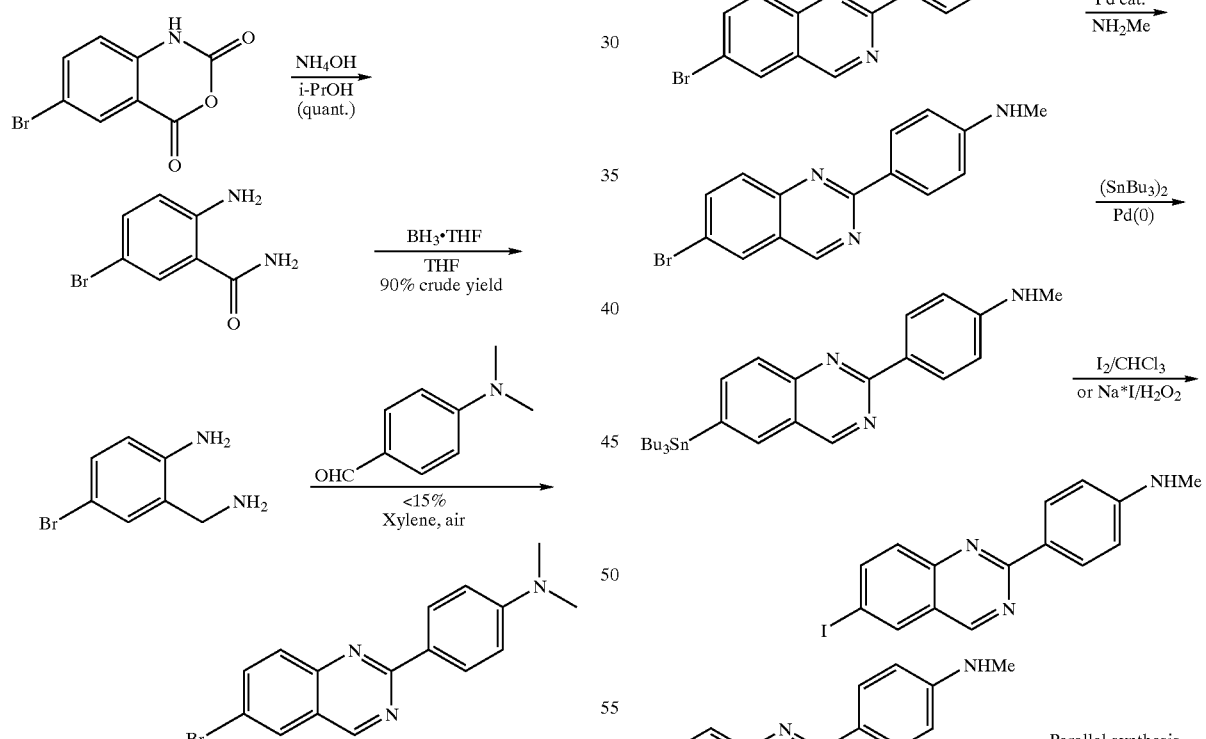
SCHEME 19
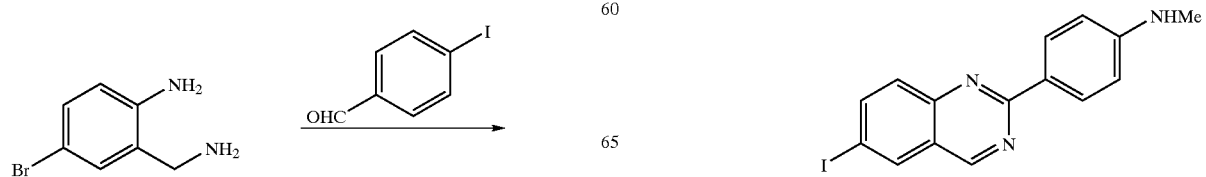

E: CH$_3$, C$_2$H$_5$, C$_3$H$_7$, C$_4$H$_9$, C$_3$H$_6$F, C$_4$H$_8$F or 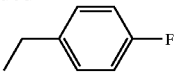

Scheme 20 depicts the synthesis of metal-chelated complexes of the present invention, where R$^9$ is as defined above, and Ar is a bicyclic system selected from the group comprising: benzothiazyl, benzoxazolyl, benzimidazolyl, benzofuranyl, imidazo[1,2a]pyridyl, and benzopyrimidyl.

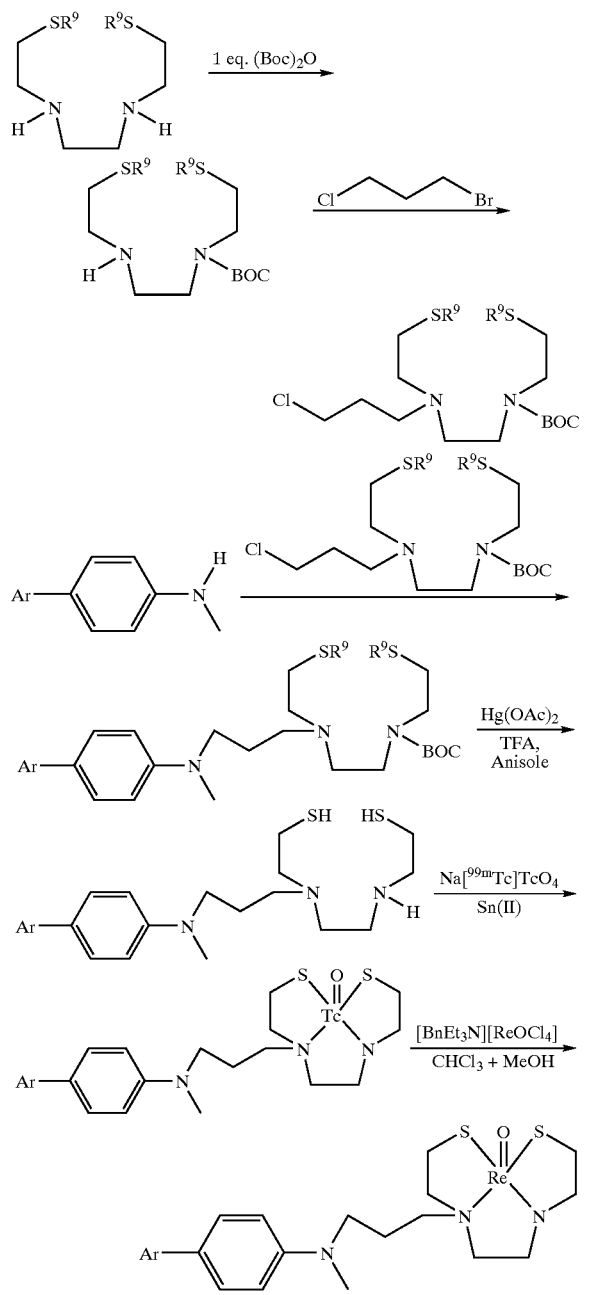

SCHEME 20

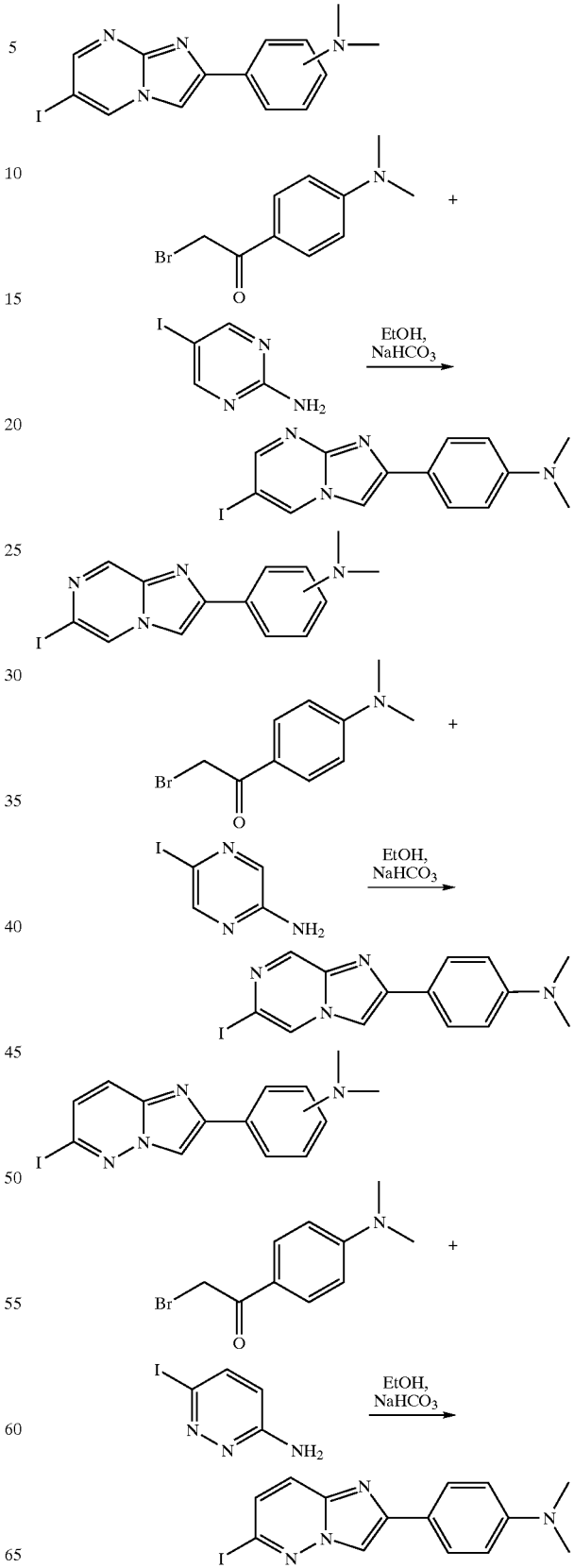

SCHEME 21

Shemes 21 through 23 are directed to imidazo[1,2a][1,3]diazepine derivatives of Formula III'.

SCHEME 22

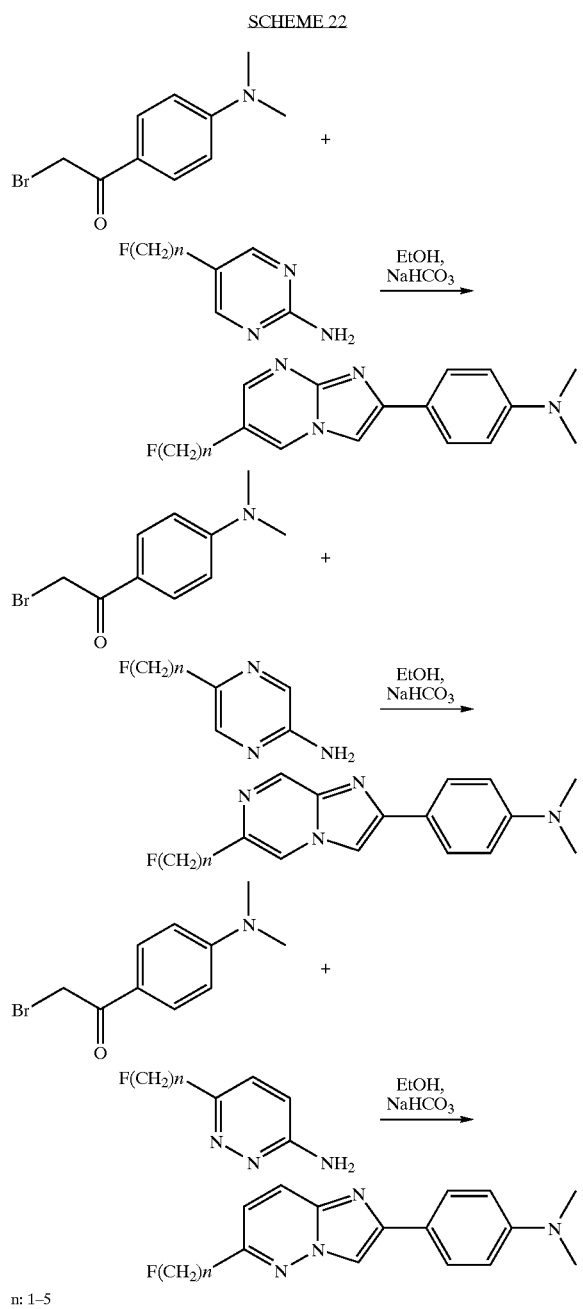

n: 1–5

SCHEME 23

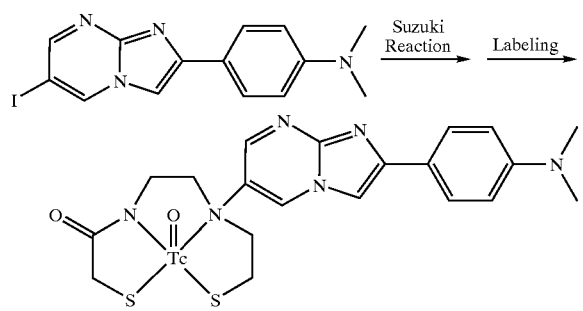

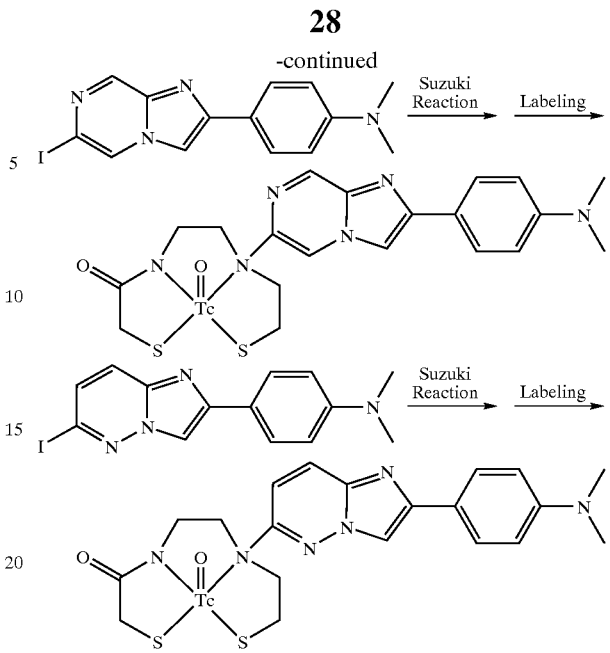

When the compounds of this invention are to be used as imaging agents, they must be labeled with suitable radioactive halogen isotopes. Although $^{125}$I-isotopes are useful for laboratory testing, they will generally not be useful for actual diagnostic purposes because of the relatively long half-life (60 days) and low gamma-emission (30–65 Kev) of $^{125}$I. The isotope $^{123}$I has a half life of thirteen hours and gamma energy of 159 KeV, and it is therefore expected that labeling of ligands to be used for diagnostic purposes would be with this isotope. Other isotopes which may be used include $^{131}$I (half life of 2 hours). Suitable bromine isotopes include $^{77}$Br and $^{76}$Br.

The radiohalogenated compounds of this invention lend themselves easily to formation from materials which could be provided to users in kits. Kits for forming the imaging agents can contain, for example, a vial containing a physiologically suitable solution of an intermediate of Formula I, II, III or III' in a concentration and at a pH suitable for optimal complexing conditions. The user would add to the vial an appropriate quantity of the radioisotope, e.g., Na$^{123}$I, and an oxidant, such as hydrogen peroxide. The resulting labeled ligand may then be administered intravenously to a patient, and receptors in the brain imaged by means of measuring the gamma ray or photo emissions therefrom.

Since the radiopharmaceutical composition according to the present invention can be prepared easily and simply, the preparation can be carried out readily by the user. Therefore, the present invention also relates to a kit, comprising:

(1) A non-radiolabeled compound of the invention, the compound optionally being in a dry condition; and also optionally having an inert, pharmaceutically acceptable carrier and/or auxiliary substances added thereto; and (2) a reducing agent and optionally a chelator;
wherein ingredients (1) and (2) may optionally be combined; and
further wherein instructions for use with a prescription for carrying out the above-described method by reacting ingredients (1) and (2) with technetium-99m in the form of a pertechnetate solution may be optionally included.

Examples of suitable reducing agents and chelators for the above kit have been listed above. The pertechnetate solution can be obtained by the user from a molybdenum-technetium generator. Such generators are available in a number of institutions that perform radiodiagnostic procedures. As noted above the ingredients (1) and (2) may be combined, provided they are compatible. Such a monocomponent kit, in which the combined ingredients are preferably lyophilized, is excellently suitable to be reacted by the user with the pertechnetate solution in a simple manner.

When desired, the radioactive diagnostic agent may contain any additive such as pH controlling agents (e.g., acids, bases, buffers), stabilizers (e.g., ascorbic acid) or isotonizing agents (e.g., sodium chloride).

The term "pharmaceutically acceptable salt" as used herein refers to those carboxylate salts or acid addition salts of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. Also included are those salts derived from nontoxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, propionate, pivalate, cyclamate, isethionate, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., *Pharmaceutical Salts, J. Pharm. Sci.* 66:1–19 (1977) which is incorporated herein by reference.)

In the first step of the present method of imaging, a labeled compound of Formula I, II, III or III' is introduced into a tissue or a patient in a detectable quantity. The compound is typically part of a pharmaceutical composition and is administered to the tissue or the patient by methods well known to those skilled in the art.

For example, the compound can be administered either orally, rectally, parenterally (intravenous, by intramuscularly or subcutaneously), intracisternally, intravaginally, intraperitoneally, intravesically, locally (powders, ointments or drops), or as a buccal or nasal spray.

In a preferred embodiment of the invention, the labeled compound is introduced into a patient in a detectable quantity and after sufficient time has passed for the compound to become associated with amyloid deposits, the labeled compound is detected noninvasively inside the patient. In another embodiment of the invention, a labeled compound of Formula I, II, III or III' is introduced into a patient, sufficient time is allowed for the compound to become associated with amyloid deposits, and then a sample of tissue from the patient is removed and the labeled compound in the tissue is detected apart from the patient. In a third embodiment of the invention, a tissue sample is removed from a patient and a labeled compound of Formula I, II, III or III' is introduced into the tissue sample. After a sufficient amount of time for the compound to become bound to amyloid deposits, the compound is detected.

The administration of the labeled compound to a patient can be by a general or local administration route. For example, the labeled compound maybe administered to the patient such that it is delivered throughout the body. Alternatively, the labeled compound can be administered to a specific organ or tissue of interest. For example, it is desirable to locate and quantitate amyloid deposits in the brain in order to diagnose or track the progress of Alzheimer's disease in a patient.

The term "tissue" means a part of a patient's body. Examples of tissues include the brain, heart, liver, blood vessels, and arteries. A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The term "patient" means humans and other animals. Those skilled in the art are also familiar with determining the amount of time sufficient for a compound to become associated with amyloid deposits. The amount of time necessary can easily be determined by introducing a detectable amount of a labeled compound of Formulae I–III' into a patient and then detecting the labeled compound at various times after administration.

The term "associated" means a chemical interaction between the labeled compound and the amyloid deposit. Examples of associations include covalent bonds, ionic bonds, hydrophilic-hydrophilic interactions, hydrophobic-hydrophobic interactions, and complexes.

Those skilled in the art are familiar with the various ways to detect labeled compounds. For example, magnetic resonance imaging (MRI), positron emission tomography (PET), or single photon emission computed tomography (SPECT) can be used to detect radiolabeled compounds. The label that is introduced into the compound will depend on the detection method desired. For example, if PET is selected as a detection method, the compound must possess a positron-emitting atom, such as $^{11}$C or $^{18}$F.

The radioactive diagnostic agent should have sufficient radioactivity and radioactivity concentration which can assure reliable diagnosis. For instance, in case of the radioactive metal being technetium-99m, it may be included usually in an amount of 0.1 to 50 mCi in about 0.5 to 5.0 ml at the time of administration. The amount of a compound of Formulae I–III' may be such as sufficient to form a stable chelate compound with the radioactive metal.

The thus formed chelate compound as a radioactive diagnostic agent is sufficiently stable, and therefore it may be immediately administered as such or stored until its use. When desired, the radioactive diagnostic agent may contain any additive such as pH controlling agents (e.g., acids, bases, buffers), stabilizers (e.g., ascorbic acid) or isotonizing agents (e.g., sodium chloride).

The imaging of amyloid deposits can also be carried out quantitatively so that the amount of amyloid deposits can be determined.

Preferred compounds for imaging include a radioisotope such as $^{123}I$, $^{125}I$, $^{131}I$, $^{18}F$, $^{76}Br$ or $^{77}Br$.

The present invention is also directed at a method of imaging amyloid deposits. One of the key prerequisites for an in vivo imaging agent of the brain is the ability to cross the intact blood-brain barrier after a bolus iv injection. The compounds of this invention possess a core ring system comprised of various substituted, fused 5- and 6-member aromatic rings. Several compounds of this invention contain a benzothiazole core and are derivatives of thioflavins. These compounds contain no quaternary ammonium ion, therefore, they are relatively small in size, neutral and lipophilic (Partition Coefficient=70 and 312 for 3 and 6a, respectively).

To test the permeability through the intact blood-brain barrier several compounds of Formula I or Emi were injected into normal mice. Initial brain uptake of 3 and 6a in mice after an iv injection was 0.67 and 1.50% dose/organ, respectively (see Table 1). The brain uptake peaked at 60 min for both compounds with a maximum brain uptake of 1.57 and 1.89% dose/organ, respectively. The blood levels are relatively low throughout the time points evaluated. For this series of ligands, specific uptake in the brain is relatively high and the retention in the brain is long.

Another aspect of the invention is a method of inhibiting amyloid plaque aggregation. The present invention also provides a method of inhibiting the aggregation of amyloid proteins to form amyloid deposits, by administering to a patient an amyloid inhibiting amount of a compound of the above Formula I, II, Those skilled in the art are readily able to determine an amyloid inhibiting amount by simply administering a compound of Formula I, II, III or III' to a patient in increasing amounts until the growth of amyloid deposits is decreased or stopped. The rate of growth can be assessed using imaging as described above or by taking a tissue sample from a patient and observing the amyloid deposits therein. The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

2-(4'-Dimethylaminophenyl)-6-iodobenzothiazole, (3)

2-(4'-Dimethylaminophenyl)-6-bromobenzothiazole (1): (Stevens, M. F. G., et al., *J. Med. Chem.* 37:1689–1695 (1994); Stevens, M. F. G., et al., PCT Int. Appl. WO19940830:47 (1995))

A mixture of 5-bromo-2-amino-benzenethiol (Mital, R. L. and Jain, S. K., *J. Chem Soc* (C):2148 (1969); Lin, A.-J. and Kasina, S., *J Heterocycl Chem* 18:759 (1981)) (306 mg, 1.5 mmol) and 4-dimethylamino benzaldehyde (224 mg, 1.5 mmol) in DMSO was heated at 180° C. for 15 min. Water (10 mL) was added after the mixture was cooled down. The solid was collected by suction and recrystallized in ethyl acetate to give 340 mg of product (68%).

$^1$H NMR (200 MHz, CDCl$_3$): δ 3.06 (s, 6H), 6.74 (d, J=9.0 Hz, 2H), 7.52 (d,d, J=8.7, 2.0 Hz, 1H), 7.82 (d, J=8.6 Hz, 1H), 7.93 (d, J=8.8 Hz, 2H), 7.95 (s, 1H).

HRMS: m/z Calcd for $C_{15}H_{14}BrN_2S(MH^+)$: 333.0061; Found: 333.0072.

2-(4'-Dimethylaminophenyl)-6-tribytylstannylbenzothiazole (2): To a solution of 2-(4'-dimethylaminophenyl)-6-bromobenzothiazole (16a) (60 mg, 0.18 mmol) in 1,4-dioxane (2 mL), toluene (2 mL) and triethylamine (2 mL) was added (Bu$_3$Sn)$_2$ (0.2 mL) followed by Pd(Ph$_3$P)$_4$ (20 mg). The mixture was stirred at 90° C. overnight. Solvent was removed and the residue was purified by PTLC (Hex:EtOAc, 6:1) to give 33 mg of product (yield 33.6%).

$^1$H NMR (200 MHz, CDCl$_3$): δ 0.90 (t, J=7.1 Hz, 9H), 1.10 (t, J=8.0 Hz, 6H), 1.34 (hex, J=7.3 Hz, 6H), 1.57 (m, 6H), 3.05 (s, 6H), 6.74 (d, J=9.0 Hz, 2H), 7.50 (d, d, J=7.9, 0.9 Hz, 1H), 7.93 (s, 1H), 7.95 (d, J=8.5 Hz, 1H), 7.97 (d, J=9.0 Hz, 2H).

HRMS: m/z Calcd for $C_{27}H_{41}N_2SSn(MH^+)$: 545.2012; Found: 545.2035.

2-(4'-Dimethylaminophenyl)-6-iodobenzothiazole, (3): To a solution of 2 (45 mg, 0.08 mmol) in CHCl$_3$ (10 mL) was added a solution of iodine (1 mL, 1M in CHCl$_3$) dropwise at RT until the color maintaining unchanged. The resulting mixture was stirred at RT for 10 min. NaHSO$_3$ solution (2 mL, 5% in water) and KF (1 mL, 1M in MeOH) were added successively. The mixture was stirred for 5 min and the organic phase was separated. The aqueous phase was extracted with CH$_2$Cl$_2$ and the combined organic phases was dried over Na$_2$SO$_4$, filtered and concentrated to give crude product which was purified by PTLC (Hex:EtOAc, 6:1) to give 9 mg of the desired product (yield 29%).

$^1$H NMR (200 MHz, CDCl$_3$): δ 3.06 (s, 6H), 6.73 (d, J=9.0 Hz, 2H), 7.69 (s, 1H), 7.70 (s, 1H), 7.93 (d, J=9.0 Hz, 2H), 8.15 (s, 1H).

HRMS: m/z Calcd for $C_{15}H_{15}N_2IS(MH^+)$: 380.9922; Found: 380.9914. Anal. ($C_{15}H_{14}N_3IS$): C, H, N.

EXAMPLE 2

2-[4'-(4''-Methylpiperazin-1-yl)-phenyl]-6-iodobenzothiazole, (6)

2-[4'-(4''-Methylpiperazin-1-yl)-phenyl]-6-bromobenzothiazole (4): The procedure described above to prepare 1 was employed to give 57.2% of product 4 from 4-(4-methylpiperazin-1-yl)benzaldehyde (Tanaka, A., et al., *J. Med. Chem.* 41:2390 (1998)) (204 mg, 1 mmol) and 5-bromo-2-amino-benzenethiol (204 mg, 1 mmol).

$^1$H NMR (200 MHz, CDCl$_3$): δ 2.38 (s, 3H), 2.60 (t, J=5.0 Hz, 4H), 3.38 (t, J=5.0 Hz, 4H), 6.96 (d, J=8.9 Hz, 2H), 7.54 (d,d, J=8.5, 1.9 Hz, 1H), 7.83 (d, J=8.5 Hz, 1H), 7.95 (d, J=8.9 Hz, 2H), 7.98 (s, 1H).

HRMS: m/z Calcd for C$_{18}$H$_{19}$BrN$_3$S(MH$^+$): 388.0483; Found: 388.0474.

2-4'-(4''-Methylpiperazin-1-yl)-phenyl]-6-tributylstannyl benzothiazole (5): The procedure described above to prepare 2 was employed, 5 was obtained in 23% yield from 4.

$^1$H NMR (200 MHz, CDCl$_3$): δ 0.89 (t, J=7.2 Hz, 9H), 1.06 (t, J=8.2 Hz, 6H), 1.30 (hex, J=7.3 Hz, 6H), 1.57 (pen, J=7.2 Hz, 6H), 2.38 (s, 3H), 2.60 (m, 4H), 3.36 (t, J=5.0 Hz, 4H), 6.96 (d, J=8.9 Hz, 2H), 7.52 (d, J=7.9 Hz, 1H), 7.93 (s, 1H), 7.95 (d, J=7.9 Hz, 1H), 7.98 (d, J=8.9 Hz, 2H).

HRMS: m/z Calcd for C$_{30}$H$_{46}$N$_3$SSn(MH$^+$): 600.2434; Found: 600.2449.

2-[4'-(4''-Methylpiperazin-1-yl)-phenyl]-6-iodobenzothiazole, (6): The same reaction as described above to prepare 3 was employed, 6 was obtained in 36% yield from 5.

$^1$H NMR (200 MHz, CDCl$_3$): δ 2.42 (s, 3H), 263 (t, J=4.8 Hz, 4H), 3.40 (t, J=4.9 Hz, 4H), 6.95 (d, J=9.0 Hz, 2H), 7.71 (s, 1H), 7.72 (s, 1H), 7.95 (d, J=8.9 Hz, 2H), 8.17 (t, J=1.0 Hz, 1H). HRMS: m/z Calcd for C$_{18}$H$_{19}$N$_3$IS(MH$^+$): 436.0344; Found: 436.0364. Anal. (C$_{18}$H$_{18}$N$_3$SI): C, H, N.

EXAMPLE 3

Preparation of 6-Tributylstannyl-2-(4'-dimethylamino-)phenyl-imidazo[1,2a]pyridine (18)

6-Bromo-2-(4'-dimethylamino-)phenyl-imidazo[1,2-a]pyridine (17)

A mixture of 2-bromo-4'-dimethylaminoacetophenone, (968 mg, 4 mmol) and 2-amino-5-bromo-pyridine (692 mg, 4 mmol) in EtOH (25 mL) was stirred under reflux for 2 hr. NaHCO3 (500 mg) was added after the mixture was cooled down. The resulting mixture was stirred under reflux for 4.5 hr. The mixture was cooled down, filtered to give 655 mg of product, 17 (52%).

$^1$H NMR (200 MHz, CDCl$_3$, δ): 3.00 (s, 6H), 6.78 (d, J=8.7 Hz, 2H), 7.17 (d,d, J=9.5, 1.7 Hz, 1H), 7.49 (d, J=9.5 Hz, 1H), 7.69 (s, 1H), 7.80 (d, J=8.7 Hz, 2H), 8.21 (d,d, J=1.7, 0.8 Hz, 1H). Anal.3a, (C$_{15}$H$_{14}$BrN$_3$).

6-Tributylstannyl-2-(4'-dimethylamino-)phenyl-imidazo[1,2-a]pyridine (18).

To a solution of 6-bromo-2-(4'-dimethylamino-)phenyl-imidazo[1,2-a]pyridine, 17, (80 mg, 0.26 mmol) in 1,4-dioxane (10 mL) and triethylamine (2 mL) was added (Bu3Sn)$_2$ (0.2 mL) in neat followed by Pd(Ph3P)$_4$ (20 mg). The mixture was stirred at 90° C. overnight. Solvent was removed and the residue was purified by PTLC (Hex:EtOAc=1:1 as developing solvent) to give 23 mg of product, 18 (17%).

$^1$H NMR (200 MHz, CDCl$_3$, δ): 0.90 (t, J=7.2 Hz, 9H), 1.10 (t, J=8.0 Hz, 6H), 1.33 (hex, J=7.1 Hz, 6H), 1.54 (pen, J=7.2 Hz, 6H), 3.00 (s, 6H), 6.78 (d, J=8.9 Hz, 2H), 7.11 (d, J=8.8 Hz, 1H), 7.57 (d, J=8.8 Hz, 1H), 7.71 (s, 1H), 7.84 (d, J=8.8 Hz, 2H), 7.95 (d, J=0.8 Hz, 1H). HRMS: m/z Calcld for C$_{27}$H$_{42}$N$_3$Sn(M++H): 528.2400; Found: 528.2402. Anal.4, (C$_{27}$H$_{41}$N$_3$Sn.2H$_2$O).

6-Iodo-2-(4'-dimethylamino-)phenyl-imidazo[1,2-a]pyridine, IMPY, (16)

A mixture of 2-bromo-4'-dimethylaminoacetophenone, (484 mg, 2 mmol) and 2-amino-5-iodo-pyridine (440 mg, 2 mmol) in EtOH (25 mL) was stirred under reflux for 2 hr. NaHCO3 (250 mg) was added after the mixture was cooled down. The resulting mixture was stirred under reflux for 4 hr. The mixture was cooled down, filtered to give 348 mg of product, 3b (48%).

$^1$H NMR (200 MHz, CDCl$_3$, δ): 3.00 (s, 6H), 6.77 (d, J=8.8 Hz, 2H), 7.27 (d, d, J=9.4, 1.5 Hz, 1H), 7.38 (d, J=9.5 Hz, 1H), 7.66 (s, 1H), 7.79 (d, J=8.8 Hz, 2H), 8.32 (d, J=0.7 Hz, 1H). Anal.3b, (C$_{15}$H$_4$IN$_3$).

EXAMPLE 4

Preparation of Radioiodinated Ligand: [$^{125}$I]IMPY, [$^{125}$I]18

The compound, [$^{125}$I]18, was prepared using iododestannylation reactions with tributyltin precursor 17. Hydrogen peroxide (50 µL, 3% w/v) was added to a mixture of 50 mL of the correspondent tributyltin precursor (1 µg/µL EtOH), 50 mL of 1N HCl and [$^{125/123}$I]NaI (1–5 mCi) in a sealed vial. The reaction was allowed to proceed for 10 min at room temperature and terminated by addition of 100 mL of sat. NaHSO$_3$. The reaction mixture was either directly extracted (styrylbenzenes) with ethylacetate (3×1 mL) or extracted after neutralization with saturated sodium bicarbonate solution (thioflavins). The combined extracts were evaporated to dryness. For styrylbenzenes the residues were dissolved in 100 µL of EtOH and purified by HPLC using a reverse phase column (Waters ubondpad, 3.9×300 mm) with an isocratic solvent of 65% acetonitrile-35% trifluoroacetic acid (0.1%) in a flow rate of 0.8 mL/min. Thioflavins were purified on a C4 column (Phenomenex Inc., Torrance, Calif.) eluted with an isocratic solvent of 80% acetonitrile-20% 3,3-dimethyl-glutaric acid (5 mM, pH 7.0) in a flow rate of 0.8 mL/min. The desired fractions containing the product were collected, condensed and re-extracted with ethylacetate. The no-carrier-added products were evaporated to dryness and re-dissolved in 100% EtOH (1 µCi/µL), The final $^{125}$I 18, with a specific activity of 2,200 Ci/mmole and a greater than 95% radiochemical purity, were stored at −20° C. up to 6 weeks for in vitro binding and autoradiography studies.

EXAMPLE 5

Partition Coefficient Determination

Partition coefficients were measured by mixing the [$^{125}$I] tracer with 3 g each of 1-octanol and buffer (0.1 M phosphate, pH 7.4) in a test tube. The test tube was vortexed for 3 min at room temperature, followed by centrifugation for 5 min. Two weighed samples (0.5 g each) from the 1-octanol and buffer layers were counted in a well counter. The partition coefficient was determined by calculating the ratio of cpm/g of 1-octanol to that of buffer. Samples from the 1-octanol layer were re-partitioned until consistent partitions of coefficient values were obtained. The measurement was done in triplicate and repeated three times.

EXAMPLE 6

Binding Assays Using Aggregated Aβ(1-40) or Aβ (1-42) peptide in solution

Figure 1B:
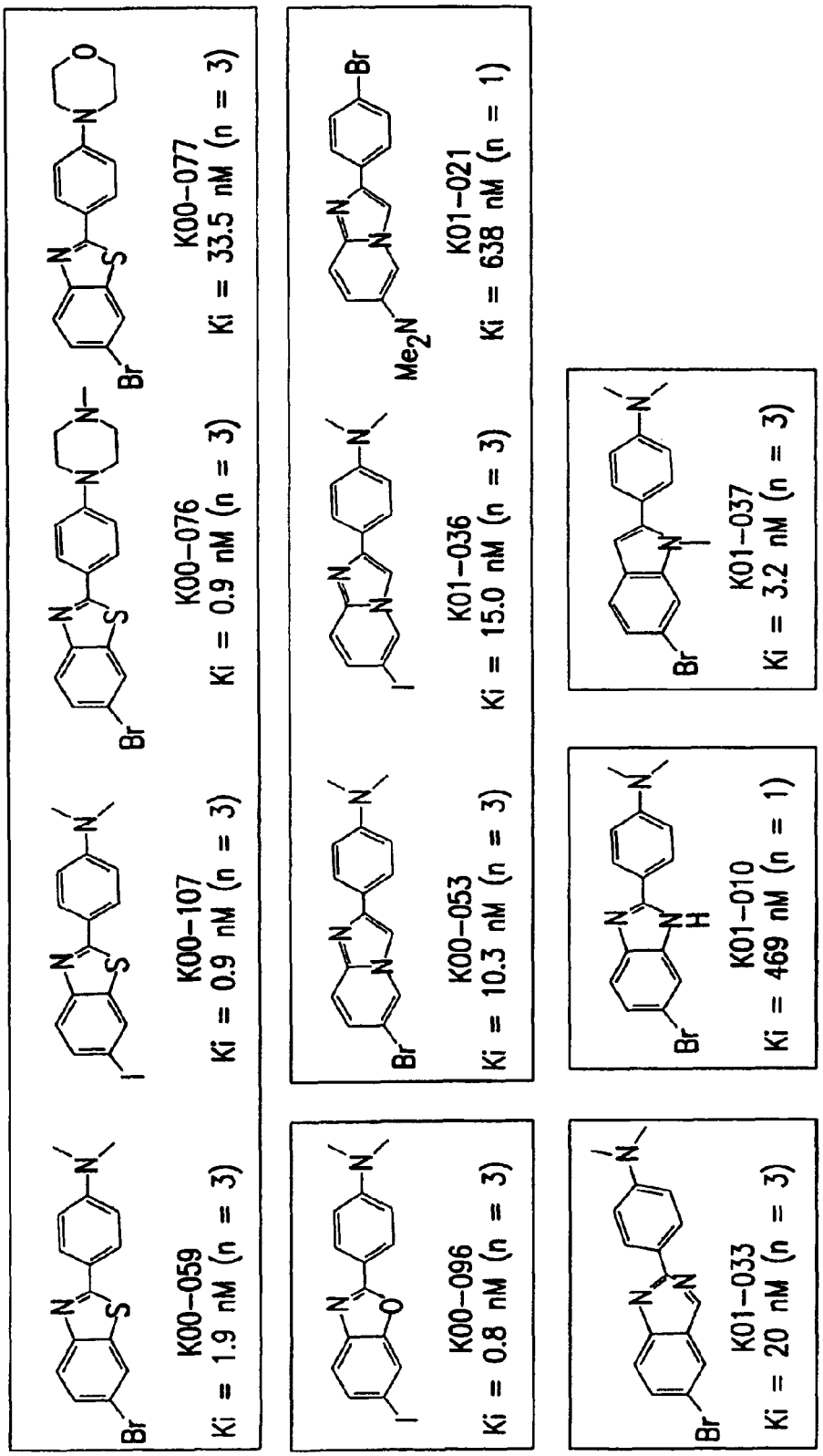

The solid forms of peptides Aβ(1-40) and Aβ(1-42) were purchased from Bachem (King of Prussia, Pa.). Aggregation of peptides were carried out by gently dissolving the peptide [0.5 mg/mL for Aβ(1-40) and 0.25 mg/mL for Aβ (1-42) in a buffer solution (pH 7.4) containing 10 mM sodium phosphate and 1 mM EDTA. The solutions were incubated at 37° C. for 36–42 h with gentle and constant shaking. Binding studies were carried out in 12×75 mm borosilicate glass tubes according to the procedure described with some modifications (Klunk, W. E., et al., *Biol. Psychiatry* 35:627 (1994)). Aggregated fibrils (10–50 nM in the final assay mixture) were added to the mixture containing 50 ml of radioligands (0.01–0.5 nM) in 40% EtOH and 10% EtOH in a final volume of 1 mL for saturation studies. Nonspecific binding was defined in the presence of 2 mM thioflavin T for thioflavins. For inhibition studies, 1 mL of the reaction mixture contained 40 ml of inhibitors (10-5–10-10 M in 10% EtOH) and 0.05 nM radiotracer in 40% EtOH. The mixture was incubated at room temperature for 3 h and the bound and the free radioactivity were separated by vacuum filtration through Whatman GF/B filters using a Brandel M-24R cell harvester followed by 2×3 mL washes of 10% ethanol at room temperature. Filters containing the bound I-125 ligand were counted in a gamma counter (Packard 5000) with 70% counting efficiency. The results of saturation and inhibition experiments were subjected to nonlinear regression analysis using software EBDA52 by which $K_d$ and $K_i$ values were calculated. Additional $K_i$ values for compounds of the invention are provided in FIG. 1A and FIG. 1B.

TABLE 1

Inhibition constants ($K_i$, nM) of compounds on ligand binding to aggregates of Aβ(1–40) and Aβ(1–42) at 25° C.

| Compounds | Aggregates of Aβ (1–40) vs[$^{125}$I]3 | Aggregates of Aβ (1–42) vs[$^{125}$I]3 |
|---|---|---|
| Chrysamine G | >1,000 | >2,000 |
| Thioflavin T | 116 ± 20 | 294 ± 40 |
| 1 | 1.9 ± 0.3 | 0.8 ± 0.3 |
| 4 | 1.6 ± 0.5 | 5.0 ± 0.8 |
| 3 | 0.9 ± 0.2 | 2.2 ± 0.4 |
| 6a | 5.4 ± 0.7 | 6.4 ± 0.7 |

Values are the mean±SEM of three independent experiments, each in duplicates.

EXAMPLE 7

In Vivo Biodistribution of New Probes in Normal Mice

While under ether anesthesia, 0.15 mL of a saline solution containing labeled agents (5–10 mCi) was injected directly into the tail vein of ICR mice (2–3 month-old, average weight 20–30 g). The mice were sacrificed by cardiac excision at various time points post injection. The organs of interest were removed and weighed, and the radioactivity was counted with an automatic gamma counter (Packard 5000). The percentage dose per organ was calculated by a comparison of the tissue counts to suitably diluted aliquots of the injected material. Total activities of blood and muscle were calculated under the assumption that they were 7% and 40% of the total body weight, respectively.

TABLE 2

| Organ | 2 min | 30 min | 60 min | 6 h | 24 h |
|---|---|---|---|---|---|
| [$^{125}$I] Compound 3 (PC = 70) | | | | | |
| Blood | 15.74 ± 6.06 | 3.26 ± 0.05 | 3.79 ± 0.19 | 1.44 ± 0.05 | 0.29 ± 0.09 |
| Heart | 1.79 ± 0.39 | 0.20 ± 0.01 | 0.17 ± 0.02 | 0.05 ± 0.01 | 0.01 ± 0.00 |
| Liver | 31.62 ± 2.38 | 10.93 ± 2.34 | 9.21 ± 3.05 | 1.52 ± 0.30 | 0.30 ± 0.07 |
| Brain | 0.67 ± 0.11 | 0.97 ± 0.29 | 1.57 ± 0.24 | 0.65 ± 0.11 | 0.04 ± 0.01 |
| [$^{125}$I] Compound 6a (PC = 312) | | | | | |
| Blood | 8.02 ± 0.82 | 5.15 ± 0.23 | 4.16 ± 0.28 | 1.49 ± 0.26 | 0.41 ± 0.09 |
| Heart | 2.19 ± 0.43 | 0.69 ± 0.02 | 0.66 ± 0.06 | 0.22 ± 0.06 | 0.08 ± 0.01 |
| Liver | 28.84 ± 3.77 | 21.22 ± 5.86 | 17.20 ± 2.49 | 5.79 ± 1.24 | 3.05 ± 0.87 |
| Brain | 1.50 ± 0.10 | 1.59 ± 0.19 | 1.89 ± 0.43 | 1.08 ± 0.08 | 0.91 ± 0.08 |
| [$^{125}$I] Compound 8 (PC = 124) | | | | | |
| Blood | 4.31 ± 0.34 | 2.80 ± 0.45 | 2.94 ± 0.18 | 2.23 ± 0.53 | 1.68 ± 0.56 |
| Heart | 1.20 ± 0.18 | 0.19 ± 0.05 | 0.11 ± 0.02 | 0.05 ± 0.00 | 0.02 ± 0.00 |
| Liver | 25.04 ± 2.45 | 17.45 ± 2.01 | 5.57 ± 0.39 | 1.08 ± 0.11 | 0.42 ± 0.08 |
| Brain | 1.43 ± 0.23 | 2.08 ± 0.03 | 1.26 ± 0.10 | 0.12 ± 0.02 | 0.01 ± 0.00 |

| Organ | 2 min | 30 min | 1 hr | 2 hr | 6 hr | 24 hr |
|---|---|---|---|---|---|---|
| [$^{125}$I]Compound 19 (PC = 100) | | | | | | |
| BLOOD | 6.41 ± 0.77 | 2.44 ± 0.36 | 2.50 ± 0.11 | 1.82 ± 0.21 | 1.40 ± 0.27 | 0.18 ± 0.02 |
| HEART | 0.79 ± 0.14 | 0.16 ± 0.02 | 0.12 ± 0.02 | 0.08 ± 0.01 | 0.04 ± 0.01 | 0.01 ± 0.00 |

TABLE 2-continued

| | | | | | | |
|---|---|---|---|---|---|---|
| MUSCLE | 13.81 ± 3.44 | 6.08 ± 0.59 | 5.03 ± 1.03 | 2.96 ± 0.84 | 1.46 ± 0.42 | 0.27 ± 0.11 |
| LUNG | 1.56 ± 0.33 | 0.31 ± 0.07 | 0.34 ± 0.08 | 0.20 ± 0.05 | 0.12 ± 0.05 | 0.05 ± 0.03 |
| KIDNEY | 4.75 ± 0.49 | 1.51 ± 0.27 | 1.17 ± 0.29 | 0.53 ± 0.05 | 0.25 ± 0.05 | 0.05 ± 0.01 |
| SPLEEN | 0.40 ± 0.06 | 0.09 ± 0.02 | 0.08 ± 0.01 | 0.05 ± 0.01 | 0.04 ± 0.01 | 0.01 ± 0.00 |
| LIVER | 20.88 ± 2.63 | 6.32 ± 0.55 | 5.88 ± 0.85 | 2.90 ± 0.21 | 1.54 ± 0.08 | 0.61 ± 0.11 |
| SKIN | 5.72 ± 0.90 | 4.69 ± 1.06 | 4.28 ± 0.25 | 3.14 ± 0.51 | 2.19 ± 0.63 | 0.22 ± 0.06 |
| BRAIN | 2.88 ± 0.25 | 0.26 ± 0.00 | 0.21 ± 0.03 | 0.14 ± 0.03 | 0.06 ± 0.02 | 0.02 ± 0.00 |

% dose/organ, average of 3 mice ± SD; Average organ weights are: blood, 2 g; muscle, 12 g; liver, g; brain 0.4 g, from which the % dose/g value for each organ or tissue can be calculated.
*(% dose/organ, avg of 3 or 4 mice ± SD)

Having now fully described this invention, it will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A pharmaceutical composition, comprising a compound of Formula III' and a pharmaceutically acceptable excipient or diluent, wherein a compound of Formula III' is selected from:

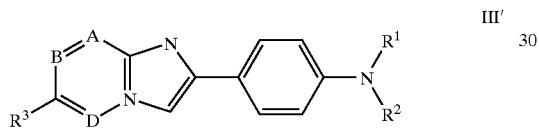

III' or a pharmaceutically acceptable salt thereof, wherein
A, B and D are CH or N,
provided that at least no more than two of A, B and D is N;
$R^3$ is Br, I, F, $^{125}$I, $^{131}$I, $^{123}$I, $^{18}$F, $^{76}$Br, $^{77}$Br, haloalkyl, Sn(alkyl)$_3$ or -L-Ch;
$R^1$ and $R^2$ are independently selected from the group consiting of hydrogen, $C_{1-4}$ alkyl, $C_{2-4}$ aminoalkyl, $C_{1-4}$ haloalkyl, haloarylalkyl, and -L-Ch, or $R^1$ and $R^2$ are taken together with the nitrogen to which they are attached to form a 5- to 7-member heterocyclic ring optionally having O, S or $NR^5$ in said ring, where $R^5$ is hydrogen or $C_{1-4}$ alkyl;
L is —(CH$_2$)$_n$—, or —(CH$_2$)$_n$—C(O)— where n is 0–5; and
Ch is a tetradentate ligand capable of complexing with a metal;
with the proviso that only one of $R^1$, $R^2$ and $R^3$ can be -L-Ch.

2. A pharmaceutical composition of claim 1, wherein A and B are CH; and
D is N.

3. A pharmaceutical composition of claim 1, wherein A and D are CH; and
B is N.

4. A pharmaceutical composition of claim 1, wherein B and D are CH; and
A is N.

5. A pharmaceutical composition of claim 2, wherein $R^1$ and $R^2$ are independently hydrogen or $C_{1-4}$ alkyl.

6. A pharmaceutical composition of claim 5, wherein $R^1$ and $R^2$ are both methyl.

7. A pharmaceutical composition of claim 6, wherein $R^3$ is Br, I, F, $^{125}$I, $^{131}$I, $^{123}$I, $^{18}$F, $^{76}$Br, $^{77}$Br, $^{18}$F/fluoro($C_{1-5}$) alkyl or Sn(alkyl)$_3$.

8. A pharmaceutical composition of claim 7, wherein $R^3$ is $^{18}$F/fluoromethyl, $^{18}$F/fluoroethyl, $^{18}$F/fluoropropyl, $^{18}$F/fluorobutyl, or $^{18}$F/fluoropentyl.

9. A pharmaceutical composition of claim 2, wherein $R^3$ is L-Ch.

10. A pharmaceutical composition of claim 9, wherein Ch is selected from the group consisting of:

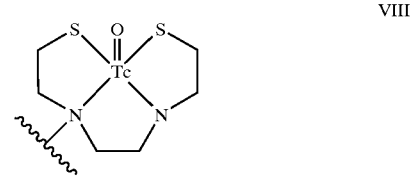

VIII

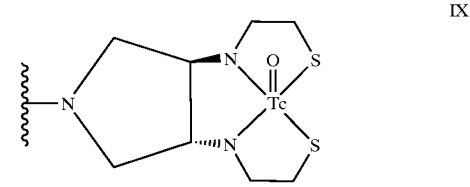

IX

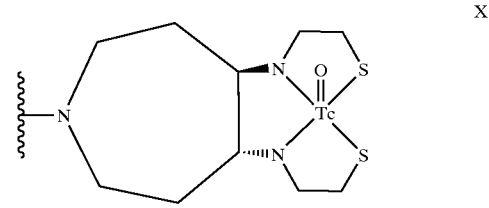

X and

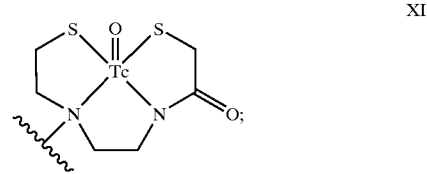

XI and
n is zero.

11. A pharmaceutical composition of claim 10, wherein Ch is:

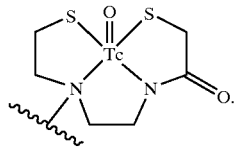

XI

12. A pharmaceutical composition of claim 11, wherein $R^1$ and $R^2$ are independently hydrogen or $C_{1-4}$ alkyl.

13. A pharmaceutical composition of claim 12, wherein $R^1$ and $R^2$ are both methyl.

14. A diagnostic composition for imaging amyloid deposits, comprising a radiolabeled compound of Formula III', wherein a radiolabeled compound of Formula III' is selected from:

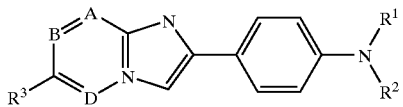

III' or a pharmaceutically acceptable salt thereof, wherein
A, B and D are CH or N,
provided that at least no more than two of A, B and D is N;

$R^3$ is $^{125}I$, $^{131}I$, $^{123}I$, $^{18}F$, $^{76}Br$, $^{77}Br$, $^{18}F(C_{1-5})$alkyl or -L-Ch;

$R^1$ and $R^2$ are independently selected from the group consiting of hydrogen, $C_{1-4}$ alkyl, $C_{2-4}$ aminoalkyl, $C_{1-4}$ haloalkyl, haloarylalkyl, and -L-Ch, or $R^1$ and $R^2$ are taken together with the nitrogen to which they are attached to form a 5- to 7-member heterocyclic ring optionally having O, S or $NR^5$ in said ring, where $R^5$ is hydrogen or $C_{1-4}$ alkyl;

L is —$(CH_2)_n$—, or —$(CH_2)_n$—C(O)— where n is 0–5; and

Ch is a tetradentate ligand complexed with a radiolabeled metal;

with the proviso that only one of $R^1$, $R^2$ and $R^3$ can be -L-Ch.

15. A method of inhibiting amyloid plaque aggregation in a mammal, comprising administering a composition of claim 1 in an amount effective to inhibit amyloid plaque aggregation.

16. A method of imaging amyloid deposits, comprising:
   a. introducing into a mammal a detectable quantity of a diagnostic composition of claim 14; and
   b. allowing sufficient time for the labeled compound to become associated with amyloid deposits; and
   c. detecting the labeled compound associated with one or more amyloid deposits.

* * * * *